Figure 1:
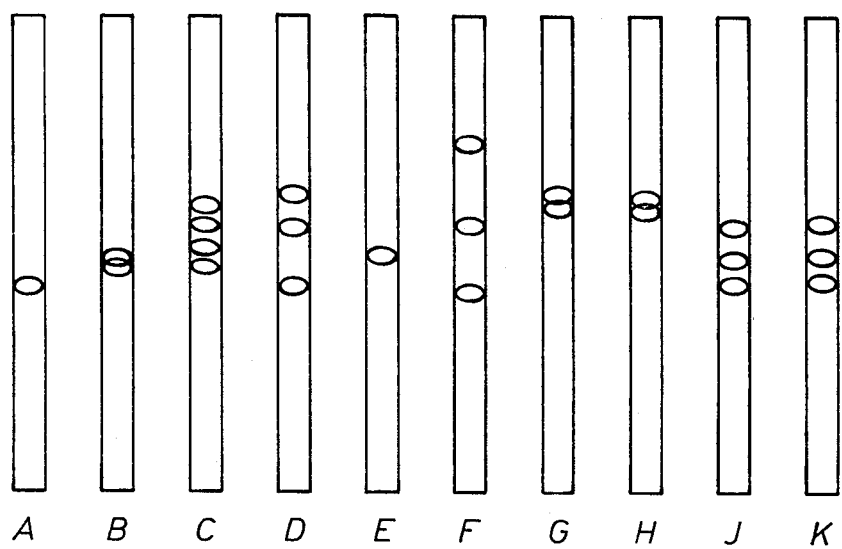

United States Patent [19]

Schnabel et al.

[11] 4,153,687

[45] May 8, 1979

[54] DERIVATIVES, HAVING AN INHIBITORY ACTION AGAINST PROTEASE AND AN ANTIPHLOGISTIC ACTION, OF THE TRYPSIN-KALLIKREIN INHIBITOR OBTAINED FROM CATTLE ORGANS (BPTI), THEIR PREPARATION AND THEIR USE AS MEDICAMENTS

[75] Inventors: Eugen Schnabel; Gerd Reinhardt; Horst D. Schlumberger, all of Wuppertal; Ernst Truscheit, Doernberg; Harald Tscheschl, Bielfeld, all of Fed. Rep. of Germany

[73] Assignee: Bayer Aktiengesellschaft, Leverkusen, Fed. Rep. of Germany

[21] Appl. No.: 847,886

[22] Filed: Nov. 2, 1977

[30] Foreign Application Priority Data

Nov. 29, 1976 [DE] Fed. Rep. of Germany ....... 2654124

[51] Int. Cl.$^2$ ..................... A61K 37/00; C07C 103/52
[52] U.S. Cl. .............................. 424/177; 260/112.5 R
[58] Field of Search .................. 260/112.5 R; 424/177

[56] References Cited

PUBLICATIONS

Annals of New York Academy of Science, vol. 146, pp. 361-787 (1968).

*Primary Examiner*—Delbert R. Phillips
*Attorney, Agent, or Firm*—Sprung, Felfe, Horn, Lynch & Kramer

[57] ABSTRACT

The invention provides derivatives of kallikrein-trypsin inhibitor (BPTI) in which one or both of the 10- or 21-tyrosine residues are linked, in the o-position relative to the phenolic hydroxyl group, to an aptionally substituted carbocyclic or heterocyclic aromatic radical via an azo group and the other if only one of the said residues is substituted is either unsubstituted or carries a nitro group or an amino group in the o-position relative to the phenolic hydroxyl group.

The azo-BPTI derivatives of the invention can be used, as medicaments for the therapy of diseases which are caused either by over-production of proteases as a result of increased liberation from the zymogens or of release during cell decomposition or by a deficiency or lack of natural indogenous inhibitors of these enzymes in organs and tissue fluids. Diseases which have this type of etiology are the various forms of shock and post-traumatic or post-operative complications, disorders in blood clotting and acute and chronic inflammatory reactions and, in particular, also chronic inflammatory reactions with necrotic and degenerative damage to connective tissue, such as pancreatitis and also vasculitides, glomerulonephritides, rheumatoid arthritis and other collagenoses caused by immune complexes and also arthritides caused by deposits due to metabolic processes (gout), but also degenerative changes in the elastic elements of vascular walls (arterioscleroses) or in the lung (pulmonary emphysema).

17 Claims, 8 Drawing Figures

DERIVATIVES, HAVING AN INHIBITORY ACTION AGAINST PROTEASE AND AN ANTIPHLOGISTIC ACTION, OF THE TRYPSIN-KALLIKREIN INHIBITOR OBTAINED FROM CATTLE ORGANS (BPTI), THEIR PREPARATION AND THEIR USE AS MEDICAMENTS

The present invention relates to new derivatives of trypsin-kallikrein inhibitor, obtainable from cattle organs, which is called BPTI (basic pancreatic trypsin inhibitor [Kunitz]) in the text which follows, and to processes for the preparation of these derivatives from natural BPTI or from derivatives of BPTI.

It has already been disclosed that BPTI [H. Kraut, E. K. Frey and E. Werle, Z. Physiol. Chem., 189, 97 (1930)], which is also termed the Kunitz inhibitor [M. Kunitz and H. H. Northrop, J. (en. Physiol. 19, 991 (1936)], inhibits a number of physiologically significant enzymes, such as, for example, kininogenins (kininogenases), plasmin, chymotrypsin and trypsin (E. Werle in W. Brendel and G. L. Haberland; Neue Aspekte der Trasylol-Therapie (New Aspects of Trasylol Therapy), 5, 9, F. K. Schattauer-Verlag Stuttgart-New York 1972; and H. Fritz, H. Tschesche, L. J. Greene and E. Truscheit (editors): Proteinase Inhibitors (Bayer Symposion V) Proc. 2nd International Research Conference, Springer-Verlag Berlin-Heidelberg-New York 1974). BPTI is employed as aprotinin (generic name) for the therapy and prophylaxis of states of shock and for the prophylaxis of post-operative and post-traumatic complications.

It is furthermore known that the exposed histidine and tyrosine residues of proteins couple with diazonium compounds to give azo derivatives [H. Pauly, Hoppe-Seyler's Z. physiol. Chem. 42, 517 (1904); ibidem 94, 288 (1915); and compare L. A. Cohen in Ann.Rev.Biochem. 37, 695 (1968)]. According to Gundlach et al. [G. Gundlach, C. Köhne and F. Turba, Biochem. Z. 336, 215 (1962)] lysine residues are also modified in this procedure. In addition, as experiments on model compounds show, α-amino groups can undergo deamination [H. Zahn, B. Wollemann and O. Waschka; Hoppe-Seyler' 5%. physiol. Chem. 294, 100 (1954)]; a reaction with the guanido groups of arginine residues has also been observed [A. N. Howard and F. Wild, Biochem. J. 65, 651 (1957)].

The present invention provides derivatives of kallikrein-trypsin inhibitor (BPTI) in which the 10- and/or 21- tyrosine residue is linked, in the ortho-position relative to the phenolic hydroxyl group, to an optionally substituted carbocyclic or heterocyclic aromatic radical via an azo group. Possible substituents are alkyl, alkoxy, sulfonic, sulfonyl, carboxyl, nitro, cyano, trifluoromethyl, chloro groups or atoms. Preferred heterocyclic aromatic radicals are aminotriazoles, aminothiazoles and aminotetrazole. More specifically, the invention provides derivatives of kallikrein-trypsin inhibitor (BPTI) in which one or both of the 10- or 21-tyrosine residues are linked, in the o-position relative to the phenolic hydroxyl group, to an optionally substituted carboxyclic or heterocyclic aromatic radical via an azo group and in case that only one of the tyrosine residues is substituted the other of the said residues is either unmodified or carries a nitro group or an amino group in the o-position relative to the phenolic hydroxyl group. The abovementioned carbocyclic or heterocyclic aromatic radicals can be mononuclear or polynuclear and can in turn be unsubstituted or carry several substituents of the first and/or second order.

In addition to BPTI, a number of BPTI derivatives, for example the BPTI derivatives which follow, can be used for the preparation of the substances according to the invention, namely:

1. Derivatives of BPTI which are partially or completely deamidised.
2. Derivatives of BPTI, the 10- or 21- tyrosine residues of which carry a nitro or an amino group in the o-position relative to the phenolic hydroxyl group. (B. Meloun, I. Fric and F. Sorm, European J. Biochem. 4, 112 (1967).
 2.1. Derivatives according to 2., which are additionally partially or completely deamidised.
3. Deamino derivatives of BPTI, obtainable as outlined in examples 40 and 41 of this application by reaction, in an acid medium, with agents which supply nitrosyl ions or by reaction, in an acid, neutral and alkaline medium, with diazotised heterocyclic amines.
 3.1. Derivatives according to 3., which are additionally partially or completely deamidised.
 3.2. Derivatives according to 3., the 10- or 21-tyrosine residues of which carry a nitro or an amino group in the o-position relative to the phenolic hydroxyl group.
 3.3. Derivatives according to 3.2., which are additionally partially or completely deamidised.
4. Derivatives of BPTI, the amino groups of which are partially or completely substituted, preferably by a modifying agent which is well known in protein chemistry, for example guanidated or amidinated or carbamylated or acylated, in particular succinylated or ethoxyformylated or alkylated.
 4.1. Derivatives according to 4., which are additionally partially or completely deamidised.
 4.2. Derivatives according to 4., the 10- or 21-tyrosine residues of which carry a nitro or amino group in the o-position relative to the phenolic hydroxyl group.
 4.3. Derivatives according to 4., the unmodified amino groups of which are additionally partially or completely deaminated.
 4.4. Derivatives according to 4.1., the 10- or 21-tyrosine residues of which carry a nitro or amino group in the o-position relative to the phenolic hydroxyl group.
 4.5. Derivatives according to 4.1, the unmodified primary amino groups of which are additionally, partially or completely deaminated.
 4.6. Derivatives according to 4.2., the unmodified primary amino groups of which are additionally, partially or completely deaminated.
 4.7. Derivatives according to 4.4., the unmodified primary amino groups of which are additionally, partially or completely deaminated.
5. Diazonium compounds of BPTI, which are obtained by diazotisation from derivatives of BPTI, the 10- and/or 21-tyrosine residues of which carry an amino group in the o-position relative to the phenolic hydroxyl group.
 5.1. Derivatives according to 5., which are additionally, partially or completely deamidised.
 5.2. Derivatives according to 5., which are additionally, partially or completely deaminated.
 5.3. Derivatives according to 5., the amino groups of which are partially or completely substituted, preferably by one of the modifying agents which are well known in protein chemistry, for example guanidated, amidinated, carbamylated or acylated, in particular succinylated or ethoxyformylated or alkylated.

5.4. Derivatives according to 5.2., which are additionally, partially or completely deamidised.

5.5. Derivatives according to 5.3., which are additionally, partially or completely deamidised.

5.6. Derivatives according to 5.3., the unmodified primary amino groups of which are additionally, partially or completely deaminated.

5.7. Derivatives according to 5.6, which are additionally, partially or completely deamidised.

Accordingly, the azo-BPTI derivatives according to the invention can be partially or completely deamidised and/or can carry on the 10- or 21-tyrosine residue a nitro group in the o-position relative to the phenolic hydroxyl group or can carry on the 10- or 21-tyrosine residue an amino group in the o-position relative to the phenolic hydroxyl group. Furthermore, the azo-BPTI derivatives according to the invention can be partially or completely deaminated and/or can be either guanylated amidinated, carbamylated, acylated, in particular succinilated or ethoxyformylated, or alkylated.

The azo-BPTI derivatives according to the invention are protease inhibitors; they not only inhibit chymotrypsin, plasmin, trypsin and kininogenins (kininogenases), as does BPTI, but in addition also in some cases they inhibit elastases, for example from the pancreas or granulocytes and also cathepsin G, the chymotrypsin like enzyme from granulocytes. Furthermore, they have an antiinflammatory action in experimental animal models. They can be used, according to the invention, as medicaments for the therapy of diseases which are caused either by over-production of proteases as a result of increased liberation from the zymogens or of release during cell decomposition or by a deficiency or lack of natural indogenous inhibitors of these enzymes in organs and tissue fluids. Diseases which have this type of etiology are the various forms of shock and post-traumatic or post-operative complications, disorders in blood clotting and acute and chronic inflammatory reactions and, in particular, also chronic inflammatory reactions with necrotic and degenerative damage to connective tissue, such as pancreatitis and also vasculitides, glomerulonephritides, rheumatoid arthritis and other collagenoses caused by immune complexes and also arthritides caused by deposits due to metabolic processes (gout), but also degenerative changes in the elastic elements of vascular walls (arterioscleroses) or in the lung (pulmonary emphysema).

The new azo-BPTI derivatives are obtained when BPTI or the derivatives of BPTI listed under 1-5 above are coupled with diazonium compounds. Suitable derivatives of BPTI for these coupling reactions are, for example, the mononitro-BPTI derivatives listed under 2. and 2.1 on pages 3-4, which are obtained according to B. Meloun, I. Frič and F. Šorm [Europ. J. Biochem. 4, 112 (1968)] or also, according to the invention, by directly nitrating BPTI with nitric acid, as well as the BPTI derivatives, which contain 3-aminotyrosine instead of tyrosine in position 10- and/or 21-, which can be prepared from the above mononitro-BPTI derivatives or from the dinitro-BPTI derivatives which is also described by Meloun and co-workers or from the dinitro-BPTI derivative which is accessible, according to the invention, by direct nitration, by reduction of the nitro groups in accordance with processes which are known from the literature [M. Sokolovsky, J. F. Riordan and B. L. Vallee, Biochem. Biophys. Res. Comm. 27, 20 (1967)]. However, aminotyrosyl-BPTI derivatives can also be prepared from azo-BPTI derivatives according to the invention, by reduction in a manner which is in itself known.

Further starting materials which can be used for the preparation of the azo-BPTI derivatives according to the invention are, inter alia, also deamino derivatives of BPTI, which can be completely or partially deamidised and/or which can carry on one of the two 10- or 21-tyrosine residue a nitro group in the ortho-position relative to the phenolic hydroxyl group; they can also contain on the 10- and/or 21-tryrosine residue an amino group in the ortho-position relative to the phenolic hydroxyl group. They are obtained according to German Patent Application P 26 19 246.1, from BPTI or derivatives of BPTI by one of the following processes:

(a) Reaction of same in acid solution with agents which supply nitrosyl ions, such as, for example, alkali metal nitrites or alkaline earth metal nitrites (e.g. sodium, potassium, calcium, strontium, barium nitrites), esters of nitrous as for example t-butylnitrite or the like acid or mixed anhydrides of nitrous acid, like nibosyl sulfate or nitrosylchloride, optionally in the presence of additives, for example those which influence the conformation of proteins (for example organic solvents, like dimethylformamide, hexamethylphosphoric acid biamide and dimethylsulfoxide, detergents like dodecylsulfate or guanidinium hydrochloride), in a heterogeneous or homogeneous system and working-up of the reaction mixtures by methods which are in themselves known. In this procedure, mixtures are obtained of BPTI derivatives of varying degrees of deamination, some of which have also been nitrated on the 10- and/or 21-tyrosine residue. This nitration can be repressed if the deamination reaction is carried out under an inert gas or in vacuo and/or an acceptor for electrophiles for example phenol, is added. During the working-up, the nitration can be prevented by rendering the mixture alkaline.

(b) Reaction of same in acid, neutral or alkaline solution with diazonium compounds, which are obtained by diazotising heterocyclic amines, in particular 3-amino-1,2,4-triazole or 5-aminotetrazole, and working up of the reaction mixture by methods which are in themselves known. The reaction additives, such as, for example, organic solvents, detergents and guanidinium hydrochloride, can optionally be added to the reaction mixtures. In this procedure, mixtures are obtained of BPTI derivatives with varying degrees of deamination, which are substantially lower compared to variant (a), from the absorption spectra of which it can be seen that neither have their tyrosine residues been converted to azo derivatives nor have their primary amino groups been converted to triazenes.

The coupling reactions, according to the invention, with BPTI or BPTI derivatives are, according to experience accompanied by modification of some amino groups (compare German Patent Application P 26 19 246.1). If the amino groups in BPTI or its derivatives are blocked in a reversible manner before the coupling, the reactions on the amino groups can be prevented; the protective groups can be removed again after the coupling reaction.

Citraconylation with citraconic anhydride is particularly suitable for temporarily blocking the amino groups; citraconyl groups can be split off again by allowing the protein or peptide solutions to stand in an acid medium for several hours. [H. B. F. Dixon and R. N. Perham; Biochem. J. 109, 312 (1968)]. The anhydrides of maleic acid [P. J. G. Butler et al.; Biochem. J. 103, 788 (1967)] and of 2,3-dimethylmaleic acid [H. B. F. Dixon and R. N. Perham; Biochem. J. 109, 312 (1968)] are similarly suitable. Furthermore, imido-esters [L. Wofsy and S. J. Singer; Biochem. 2, 104 (1963)] and also 2-methoxy-5-nitro-tropone [H. Tamaoki et al.; J. Biochem. 62, 7 (1967)] are suitable for protecting the primary amino groups; both protective groups can be removed by mild hydrazinolysis in a weakly basic medium [M. L. Ludwig and R. Byrne; J. Am. Chem. Soc. 84, 4160 (1962)]. Various protective groups known from peptide chemistry, above all of the urethane type, are also suitable, of which the following are chosen only as examples; in some cases they can be split off by mild acidolysis (for example the t-butoxycarbonyl group/-Boc [R. Schwyzer, P. Sieber and R. Kappeler; Helv. Chim. Acta 42, 2622 (1959)] or the isobornyloxycarbonyl group/Ibc [G. Jager and R. Geiger; Liebigs Ann. Chem. 1535 (1973)], in some cases also by mild alkalysis, for example the fluorenylmethoxycarbonyl group/-FMOC/[L. A. Carpino and G. Y. Han; J. Am. Chem. Soc. 92, 5748 (1970)] or the methylsulphonylethoxycarbonyl group/Msc [G. I. Tesser and J. C. Balvert-Geers; Int. J. Peptide Protein Res. 7, 295 (1975)], in some cases by photolysis, for example the α,α-dimethyl-3,5-dimethoxybenzyloxycarbonyl group/Ddz [C. Birr et al.; Liebigs Ann. Chem. 763, 162 (1972)] or the 2,2'-dinitrodiphenylmethoxycarbonyl group/DNBOC [A. Patchornik, B. Amit and R. B. Woodward; J. Am. Chem. Soc. 92, 6333 (1972)], and in some case also by catalytic hydrogenolysis - even in the presence of a sulphur-containing substrate- (for example the 1,1'-dimethyl-2-propinoxycarbonyl group/DMPOC [G. L. Southard, B. R. Zaborowski and J. M. Pettee; J. Am. Chem. Soc. 93, 3302 (1971)]. Furthermore, possible protective groups which are labile towards bases are also the trifluoroacetyl radical/TFA [R. F. Goldberger Methods Enzymol. 11, 317 (1967)] and the tetrafluorosuccinyl radical [V. G. Braunitzer et al., Hoppe-Seyler's Z. physiol. Chem. 349, 265 (1968)].

Furthermore, carbonyl compounds which, with the primary amino groups, form Schiff's bases, which readily decompose again in an acid medium to give the starting materials, are suitable for protecting the amino groups (E. Wunsch, in: Houben-Weyl, Methoden der organischen Chemie (Methods of Organic Chemistry), IV edition, Volume 15/1, page 277 et seq., editors: E. Muller et al., Georg Thieme Verlag, Stuttgart, 1974); thus, for example, benzaldehyde, 3-methyl-5-formyl-salicyclic acid or 2-sulphobenzaldehyde as well as β-dicarbonyl compounds, such as, for example, ethyl acetoacetate, acetylacetone or benzoylacetone.

According to the invention, it is also possible to reduce any of the abovementioned azo- or nitro groups at Tyr 10 and/or 21 of BPTI to the corresponding aminogroup in a manner which is in itself known and then to diazotise these in a manner which is in itself known and to react the resulting diazonium compounds of BPTI, in a manner which is in itself known, with compounds which are suitable for coupling. Compounds which are suitable for coupling are, for example, mononuclear or polynuclear aromatic (e.g. monocyclic carbocyclic or bicyclic carbocyclic aromatic hydroxy or amino compounds, such as phenol, naphthol, hydroxybiphenyl, aniline, etc.) hydroxy or amino compounds, which can optionally carry substituents preferably alkyl-, alkoxy-, cyano, nitro, chloro, sulfo, dialkylamino and amino substituents and heterocyclic compounds, preferably imidazole which can optionally carry substituents.

Azo-BPTI derivatives according to the invention which still contain carbonamide groups can subsequently be completely or partially deamidised by treatment with non-oxidising strong, preferably mineral acids, in particular hydrochloric acid, sulphuric acid or trifluoroacetic acid, but also organic acids may be taken. Furthermore, azo-BPTI derivatives according to the invention which still contain aliphatic amino groups can subsequently be partially or completely deaminated - in accordance with the process in German Patent Application P 26 19 246.1 - by reaction, in acid, neutral or alkaline solution, with non-coupling diazonium compounds or by reaction, in acid solution, with compounds which supply nitrosyl ions.

However, azo-BPTI derivatives according to the invention which still contain aliphatic amino groups can also subsequently be either guanylated, amidinated, carbamylated, acylated, in particular succinylated or ethoxyformylated, or alkylated.

Azo-BPTI derivatives according to the invention in which one of the tyrosine residues in position 10 or 21 can still be modified can subsequently be nitrated by reaction with tetranitromethane in a manner which is in itself known or, according to the invention, by reaction with nitric acid.

The Azo-BPTI derivatives according to the invention are obtained by coupling the BPTI derivatives listed above with diazonium compounds in an aqueous solution, which can optionally also contain inert organic solvents, such as, for example, pyridine, quinoline, dimethylformamide, dimethylsulphoxide or hexamethylphosphoric acid triamide, and/or additives, such as salts, for example guanidine hydrochloride or lithium chloride, and/or non-electrolytes, such as, for example, urea.

Depending on the reactivity of the diazonium compounds, the coupling reactions are carried out at pH values between 1 and 12, preferably at pH 5 to 11, solutions of BPTI or BPTI derivatives in water or in the solvents listed above, which optionally contain the additives indicated above, being combined with the diazonium salt solutions. The pH value of the reaction mixture is adjusted and kept constant by adding alkali metal oxides, hydroxides, carbonates or bicarbonates or alkaline earth metal oxides, hydroxides, carbonates or bicarbonates, or tertiary amines, such as, for example, triethylamine, N-metylmorpholine, triethanolamine or pyridine. However, the reactions can also be carried out in buffer solutions, in particular phosphate or borate buffers. The rates of the reactions can appropriately be controlled via the pH value of the reaction mixture, as Table I shows for the reaction of BPTI with the 3,5-dichlorobenzene-diazonium compound.

| pH value of the reaction solution | reaction time[+] |
|---|---|
| 6.0 | 24 hours |
| 7.0 | 5 hours |
| 8.0 | 2 hours |
| 9.0 | about 1 hour |
| 10.0 | 5 minutes |
| 11.0 | about 3 minutes |
| 12.0 | 3 minutes |

[+]The end point of the reaction was determined by a spot reaction, in which a sample of the reaction solution was reacted with 1-(2-aminoethylamino)-naphthalene as coupling partner.

The degree of coupling after the times indicated is about the same for all the pH values listed here.

During the coupling reactions the temperatures of the reaction mixtures are kept at about −15° C. to about 30° C., preferably at 0° C. to 10° C. In certain cases it is appropriate to first carry out the coupling at temperatures between 0° C. and 4° C. and then to increase the temperature up to about 25° C. Excess diazonium compound can optionally be bonded, by adding, for example, phenol to the reaction solution, before working up the reaction mixture. The consumption of diazonium compound during the coupling reactions can be followed with the aid of sample couplings with 1-(2-aminoethylamino)-naphthalene by spotting. In the process according to the invention, the molar ratio of diazonium compounds to BPTI or BPTI derivatives is about 1:1 to about 10:1, preferably about 1:1 to about 5:1, the concentrations of BPTI or BPTI derivatives in the solution used for coupling being about 1–30%, preferably 5–15%.

Suitable azo compounds for the preparation of the azo-BPTI derivatives according to the invention are mononuclear or polynuclear (particularly dinuclear) carbocyclic aromatic as well as heterocyclic diazonium compounds which are prepared from the corresponding amines. These can also carry one or more substituents. Derivatives of aniline are suitable in particular, for example alkylanilines, alkoxyanilines, halogen derivatives of aniline, nitroanilines, cyanoanilines, trifluoromethylanilines, acetoaminoanilines, amino-acetophenones, aminobenzenesulphonic acids, aniline-disulphonic acids, aminobenzenearsinic acids, aminobenzoic acids and aminodiphenyl ethers; particularly suitable dinuclear amines are α- and β-naphthylamine and derivatives thereof, for example aminonaphthalene sulphonic acids. Aminotriazole and aminophenyltriazole, which may be substituted, are especially suitable as heterocyclics.

The diazotisation of the amines is carried out by the customary processes [R. Putter in "Houben-Weyl, Methoden der organischen Chemie (Methods of Organic Chemistry)," Volume 10/3, page 1 et seq., editor E. Muller with the cooperation of O. Bayer, H. Meerwein and K. Ziegler, Georg Thieme Verlag, Stuttgart 1965] by reaction with compounds which supply nitrosyl ions, in particular sodium nitrite in mineral acid solution or suspension, optionally in the presence of inert organic solvents, in particular dimethylformamide, acetic acid or propionic acid, at temperatures from about −20° C. to about 50° C., preferably −5° C. to 20° C., or with nitrosylsulphuric acid or nitrosyl chloride in acetic acid/propionic acid mixtures, with the addition of mineral acid, at temperatures of, preferably, about −20° C. to 0° C. The diazotisation period is very different; it depends on the solubility of the amines and their substitution pattern and varies between a few minutes and several hours. After the diazotisation, excess nitrosyl ions are destroyed by reaction with amidosulphonic acid or urea in order to prevent deamination of the BPTI derivatives by nitrosyl ions, such as is possible while carrying out the couplings in an acid medium (compare German Patent Application P 26 19 246.1).

Mixtures of various components are obtained during the coupling of BPTI or BPTI derivatives with the azo-diazonium compounds. The composition of these azo-BPTI derivative mixtures can be controlled by choosing the reaction conditions, in particular via the ratio of BPTI or BPTI derivative employed for the coupling and the diazonium compound, the pH value of the reaction mixtures and the reaction period, as well as by the abovementioned additions to the reaction solutions. Furthermore, additions of this type prevent the precipitation of the azo-BPTI derivatives, which are sometimes very sparingly soluble, and make it possible for the reaction to proceed further. Thus, for example, even when 10 equivalents of diazonium compound are used, BPTI does not react with diazotised 5-amino-1H-tetrazole in aqueous solution to give the azo derivative, whilst in the presence of 4 m of urea coupling to give azo-BPTI derivatives takes place under otherwise identical conditions. After the coupling reaction has ended, the additives mentioned and other low-molecular substances can be separated off, for example by ultrafiltration, gel filtration or dialysis with acetylated dialysing tubes. The mixtures of azo-BPTI derivatives can be fractionated, for example by chromatography on ion exchangers.

If a substance mixture, which has been obtained by coupling BPTI with diazotised 3,5-dichloroaniline in accordance with Example 10, is chromatographed on SP-Sephadex C 25 which has been equilibrated with a 0.05 M ammonium acetate solution by initially eluting with a NaCl gradient and then with a 0.5 M $NH_3$ solution, various fractions are obtained which differ in their electrophoretic mobility, their quantitative amino-acid composition, their absorption spectrum and their inhibitory power against some characteristic proteases.

In contrast to BPTI, some of the azo-BPTI derivatives according to the invention inhibit elastases from the pancreas and granulocytes, as well as cathepsin G, the chymotrypsin-like enzyme from granulocytes. In respect to other proteases, such as chymotrypsin, pancreas kallikrein, plasma kallikreins, plasmin and trypsin, the inhibition spectra for the individual derivatives differ qualitatively and/or quantitatively from those of BPTI. The inhibition of elastase is not the blocking of the substrate described by J. Pütter and G. Schmidt-Kastner [Biochem. Biophys. Acta 127, 538 (1966)], which takes place only with very high BPTI concentrations, but is an inhibition of the enzyme.

This inhibitory action against elastase is the more surprising since it follows from the current state of the art [D. M. Blow, C. S. Wright, D. Kukla, A. Ruhlmann, W. Steigemann and R. Huber, J. Mol. Biol. 69, 137 (1972); R. Huber, D. Kukla, W. Steigemann, J. Deisenhofer and A. Jones in H. Fritz, H. Tschesche, L. J. Greene and E. Truscheit (editors), Proteinase Inhibitors (Bayer-Symposium V) Proc. 2nd Intern. Res. Conference, page 484, Springer-Verlag Berlin-Heidelberg-New York 1974] that BPTI is accomodated via its active centre (lysine-15 resudue), in the nature of a substrate in the specificity pocket of the enzymes which can be inhibited and thus blocks the enzyme activity. Even when the side chain of the lysine-15 residue is deaminated in all of the derivatives according to the invention, it is not to be expected, according to the current state of knowledge, that it would fit into the relatively small specificity pocket of the elastases, (D. Shotton in H. Fritz and H. Tschesche (editors), Proceedings of the International Research Conference on Proteinase Inhibitors, page 47, Walter de Gruyter, Berline-New York 1971).

The azo-BPTI derivatives according to the invention are new. They can be characterised and differentiated from known substances by chemical, physico-chemical, biochemical and biological properties. Use has been made of the following criteria:

(1) Amino-acid composition

The amino-acid composition was determined according to S. Moore, D. H. Spackmann and W. H. Stein [Anal. Chem. 30, 1185 (1958)]. The values of some amino-acid residues for several characteristic azo-BPTI derivatives are given in Table 2 the content of which is changed by the coupling reactions according to the invention.

(2) Electrophoretic properties (disc electrophoresis)

Disc electrophoreses were carried out in a 15% separating gel with the buffer system III, such as is described by O. Gabriel in Methods Enzymol. XXII, 565 (1971). The current was 3 mA per tube; the electrophoresis was stopped as soon as the marker dyestuff (methyl green) had completely migrated through the gel. After the separation, the gels were stained for 30 minutes with a 0.1% solution of Amido Black in 7% acetic acid. Excess dyestuff was then removed again with 7% acetic acid. FIG. 1 represents characteristic disc electropherograms.

In FIG. 1 (see attached) the electropherograms of the following substances are compared:
A: BPTI
B: BPTI derivative according to Example 44
C: BPTI derivative according to Example 45
D: BPTI derivative according to Example 46
E: BPTI derivative according to Example 47
F: BPTI derivative according to Example 48
G: BPTI derivative according to Example 49
H: BPTI derivative according to Example 50
I: BPTI derivative according to Example 51
K: BPTI derivative according to Example 52 which can be stained with ninhydrin, are eluted together with glycine and/or alanine and these then simulate higher glycine contents and/or alanine contents.

(3) An amino-acid analysis of BPTI was recorded for comparison.
The theoretical values of the particular amino-acids are: Gly and Ala and Arg = 6,0; Tyr and Lys = 4,0

(4) Nitrotyrosine was also found to the extent of 2.01.

(3) Absorption spectra

The absorption spectra are particularly suitable for characterising the azo-BPTI derivatives according to the invention. Characteristic absorption maxima, which, however, sometimes only show as shoulders, occur at 470–500 nm and at 325 nm in a 0.1 M tris buffer of pH 9.0 and 0.1 M sodium hydroxide solution and at 380 nm and 325 nm in a 0.1 M acetate buffer of pH 4.5. Nitro groups can also be detected in the absorption spectra of the azo derivatives of nitro-BPTI derivatives. The absorption spectra of some azo-BPTI derivatives according to the invention are represented in FIGS. 2–4.

Figure 2:
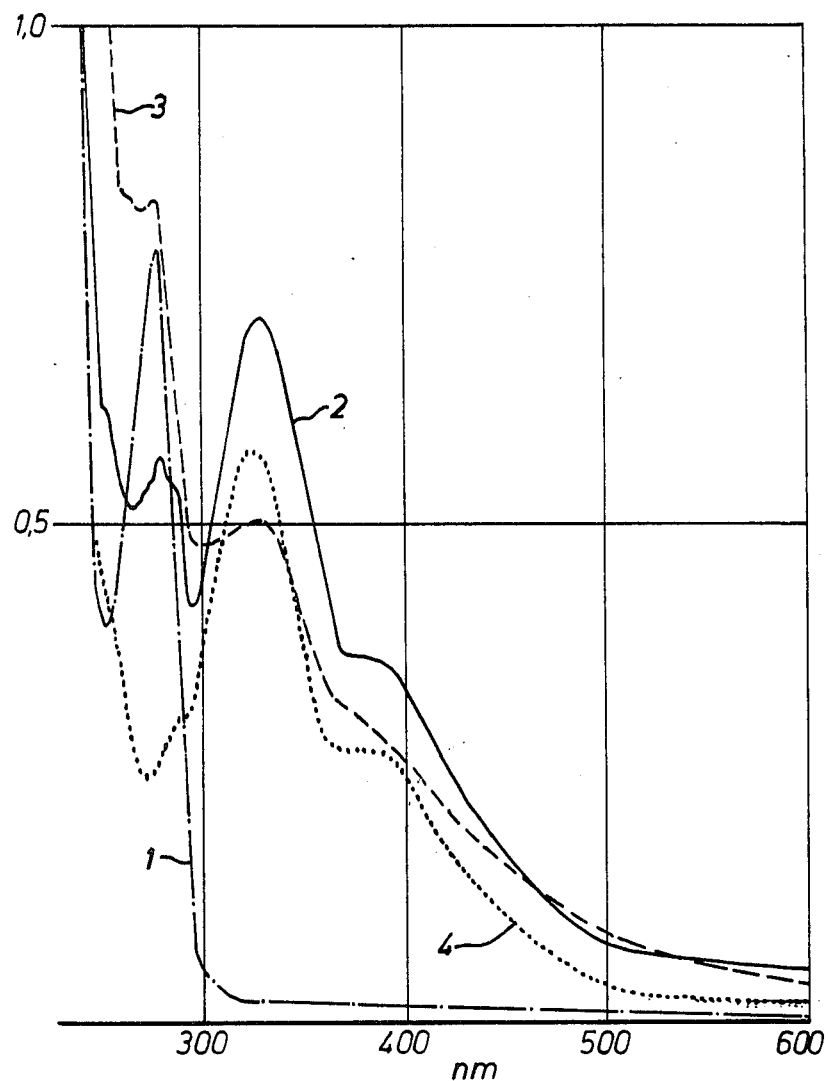

FIG. 2 shows the absorption spectra of BPTI and some azo-BPTI derivatives according to the invention in a 0.1 molar acetate buffer of pH 4.5. The curves 1 to 4 in FIG. 2 are attributed to the following compounds:
1. BPTI
2. Azo-BPTI derivative according to Example 5
3. Azo-BPTI derivative according to Example 13 and
4. Azo-BPTI derivative according to Example 48.

Figure 3:
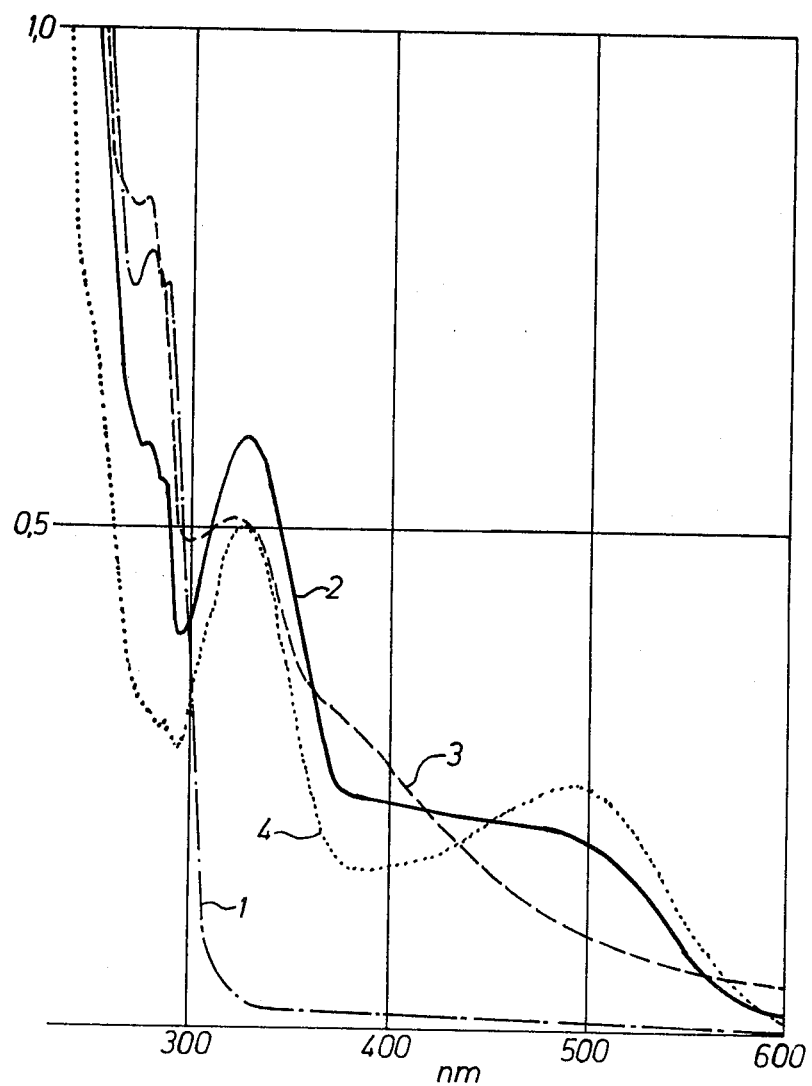
Figure 4:
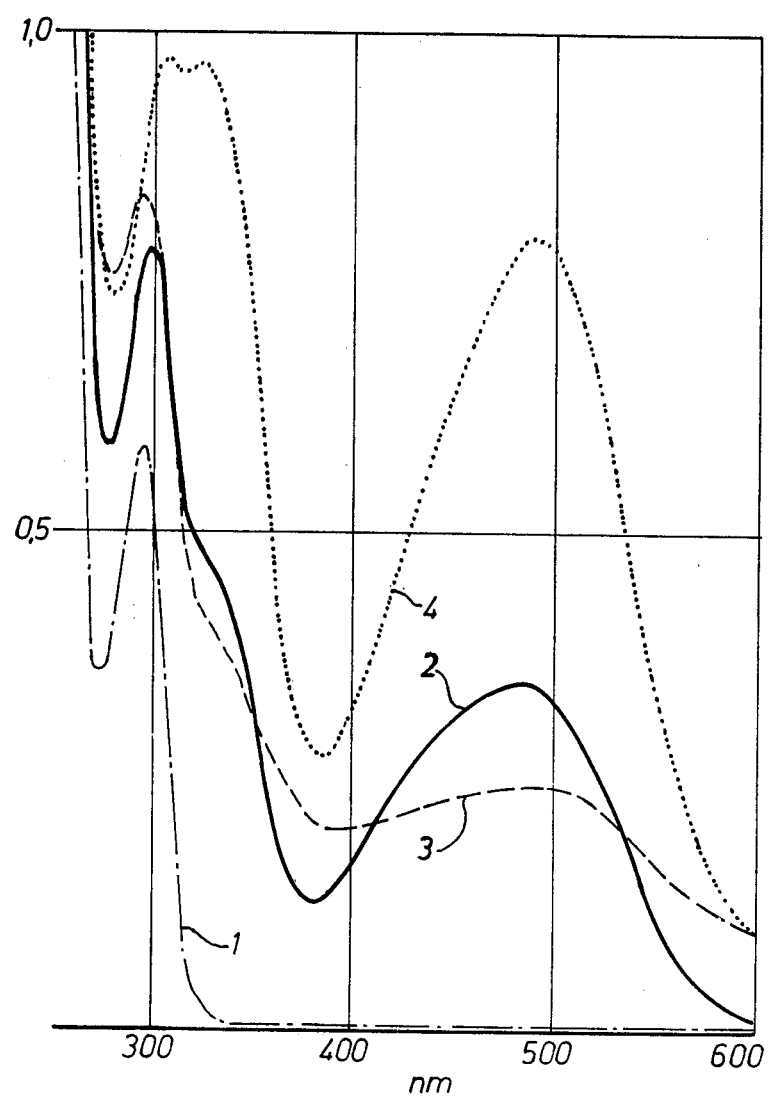

FIG. 3 shows the absorption spectra of BPTI and some azo-BPTI derivatives according to the invention in a 0.1 molar tris buffer solution, at pH 9.0.

The curves 1 to 4 in FIG. 3 denote:
1. BPTI,
2. Azo-BPTI derivative according to Example 5, Table 1

| Contents of characteristic amino-acids determined by amino-acid analysis of some azo-BPTI derivatives. | | | | | |
|---|---|---|---|---|---|
| Azo-BPTI derivatives prepared according to Example | of amino-acid residue mol | | | of azo-BPTI derivative[1] | |
| | glycine[2] | alanine[2] | tyrosine | lysine | arginine |
| BPTI | 6.09 | 6.00 | 3.80 | 4.08 | 6.01 |
| 3 | 6.11 | 5.64 | 3.49 | 3.37 | 5.68 |
| 5 | 6.28 | 6.00 | 3.06 | 3.52 | 5.87 |
| 7 | 6.36[2] | 6.00 | 3.29 | 3.40 | 5.80 |
| 9 | 5.75 | 5.99 | 3.25 | 2.56 | 5.11 |
| 12 | 5.70 | 6.69[2] | 3.47 | 3.38 | 4.52 |
| 17 | 5.67 | 7.27[2] | 3.43 | 3.09 | 5.81 |
| 19 | 5.80 | 6.08 | 3.38 | 3.15 | 4.68 |
| 23 | 5.70 | 5.71 | 3.40 | 3.00 | 5.73 |
| 24 | 5.79 | 5.75 | 2.81 | 1.59 | 5.42 |
| 35 | 5.30 | 5.65 | 3.35 | 2.89 | 5.66 |
| 38 | 5.60 | 6.11 | 3.41 | 2.61 | 4.49 |
| 39 | 5.83 | 5.81 | 3.25 | 2.11 | 5.81 |
| 42 | 5.48 | 5.78 | 1.23[4] | 3.23 | 5.63 |
| 44 | 5.81 | 5.84 | 3.02 | 3.92 | 5.80 |
| 45 | 5.66 | 5.70 | 2.46 | 3.67 | 5.58 |
| 46 | 5.65 | 5.67 | 3.22 | 3.68 | 5.63 |
| 48 | 5.73 | 5.82 | 2.43 | 3.67 | 5.93 |
| 50 | 5.77 | 5.80 | 3.20 | 3.60 | 5.90 |
| 52 | 5.58 | 5.88 | 3.00 | 3.59 | 5.79 |
| 53 | 5.72 | 6.12 | 1.36 | 3.90 | 5.59 |
| 55 | 5.74 | 5.82 | 3.67 | 3.29 | 5.85 |

Description of Table 2

(1) The molecular weight of the derivatives was assumed to be 6 511, as for natural BPTI.

(2) The alanine content and glycine content serve as an internal standard. Depending on the elution conditions for the amino-acid analysis, unknown substances, 3. Azo-BPTI derivative according to Example 13 and
4. Azo-BPTI derivative according to Example 48.

FIG. 4 shows the absorption spectra of BPTI and some azo-BPTI derivatives according to the invention in a 0.1 molar sodium hydroxide solution.

The curves 1 to 4 in FIG. 4 denote:

1. BPTI,
2. Azo-BPTI derivative according to Example 5,
3. Azo-BPTI derivative according to Example 13 and
4. Azo-BPTI derivative according to Example 48.

Figure 5:
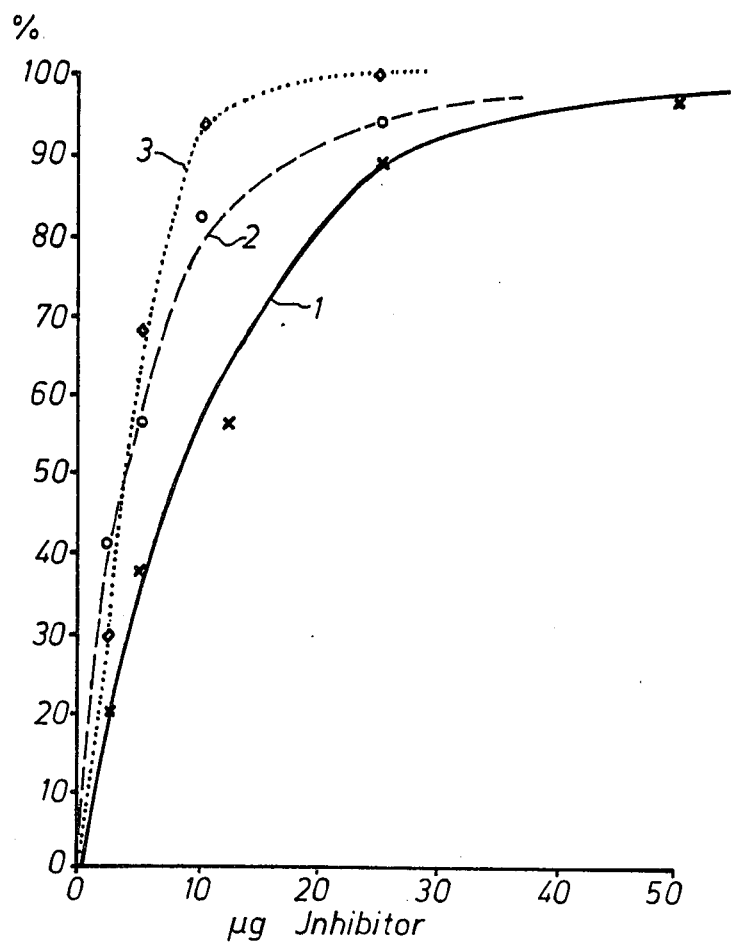

(4) Protease inhibition spectrum
(a) Elastase inhibition
(a) Pancreas elastase inhibition Crystallised pancreas elastase (pig) from Messrs. Nutritional Biochemicals Corp. was used for the inhibition tests with the azo-BPTI derivatives according to the invention. Elastin-Congo Red [M. A. Naughton and F. Sanger, Biochem. J. 78, 156 (1961)], soluble elastin [S. Keller and I. Mandl, Biochem. Med. 5, 342 (1971)] and, particularly advantageously, succinyl-L-alanyl-L-alanyl-L-alanine-p-nitroanilide [J. Bieth, B. Spiess and C. G. Wermuth, Biochem. Med. 11, 350 (1974)] were used as substrates. The synthetic peptide substrate makes it possible to carry out a simple colorimetric determination of the enzyme activity employed in the test. In the elastin-Congo Red test, the amount of elastase employed was about 1.1 nkat (compare Enzyme Nomenclature, Recommendations [1972] of the International Union of Pure and Applied Chemistry and the International Union of Biochemistry, 1973, Elsevier Amsterdam-New York, page 26-27); about 0.25 nkat of elastase was employed per test when soluble elastin was used as the substrate and likewise when succinyl-L-alanyl-L-alanyl-L-alanine-p-nitroanilide was used. In order to carry out quantitative determinations of the elastase inhibition, the amounts of enzyme indicated above were added to the substrate solution to which inhibitor solutions of defined concentration had been added. In order to ensure maximum formation of the complex, the enzyme and the inhibitor in some cases were preincubated for 15 minutes before the substrate were added. In the case of elastin-Congo Red test, the hydrolysis of the substrate was determined by measuring the extinction, at 492 nm, of the soluble products of proteolysis formed after a defined time. In the case of the test with soluble elastin, the rate of hydrolysis ws ascertained by photometric determination of the products of proteolysis which had gone into solution after a defined time and which can be stained with ninhydrin. When succinyl-L-alanyl-L-alanyl-L-alanine-p-nitroanilide was used as the substrate, the hydrolysis was determined by continuous measurement of the extinction, at 410 nm, of the p-nitroaniline liberated. The inhibition values (expressed in % inhibition) were determined by subtracting the residual activity of elastase, measured after addition of the inhibitor, from the activity of the enzyme control. The inhibition values of some azo-BPTI derivatives are summarised in Tables 3 to 5. FIG. 5 shows the dependence of the elastase inhibition on the amount of three inhibitors. Other azo-BPTI derivatives according to the invention show a similar inhibition curve.

The percentage inhibition of 0.25 nkat of pancreas elastase (pig) by some of the azo-BPTI derivatives according to the invention (determined by the method of J. Bieth et al.), with a 15 minute per-incubation of the inhibitor and the enzyme) is shown in FIG. 5 (compare Table 5).

The curves 1, 2 and 3 in FIG. 5 denote:
1. Azo-BPTI derivative according to Example 7,
2. Azo-BPTI derivative according to Example 17 and
3. Azo-BPTI derivative according to Example 28.

(β) Granulocyte-elastase inhibition

The mixture of isoenzymes used for the inhibition tests was obtained from human granulocytes by the method of K. Ohlsson and I. Olsson [Europ. J. Biochem. 42, 519 (1974)]. Succinyl-L-alanyl-L-alanyl-L-alanine-p-nitroanilide [J. Bieth, B. Spiess and C. G. Wermuth, Biochem. Med. 11, 350 (1974)] is particularly suitable as the substrate. The inhibition values of some azo-BPTI derivatives are recorded in Table 6; the dependence of the inhibition on the inhibitor concentrations is given for some derivatives in FIG. 6.

Figure 6:
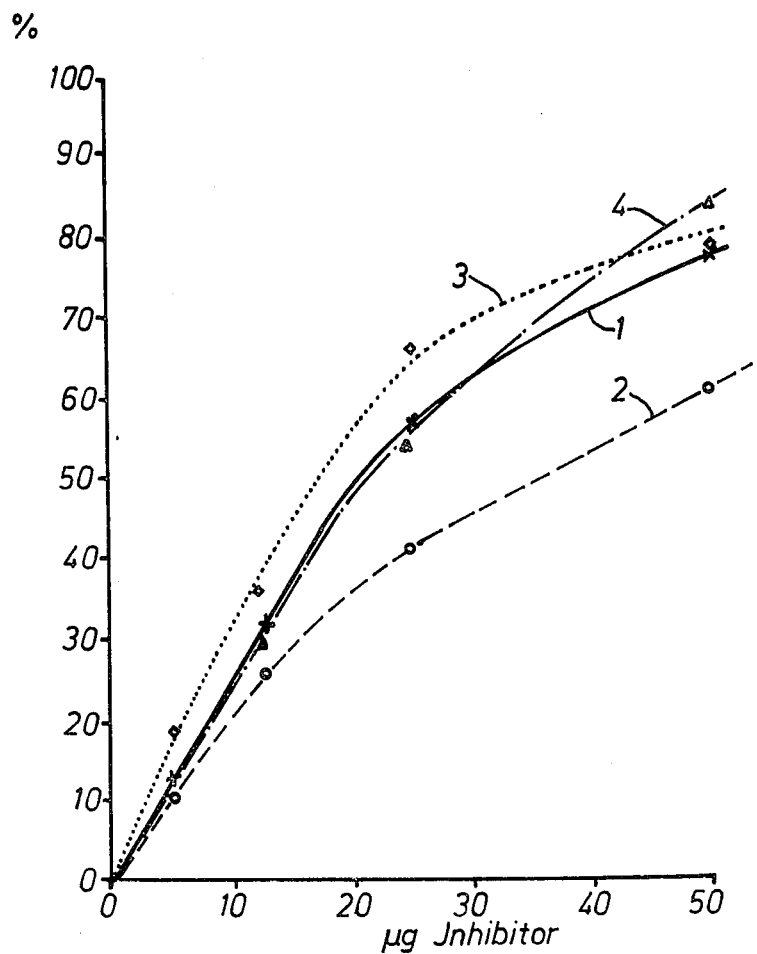
Figure 7:
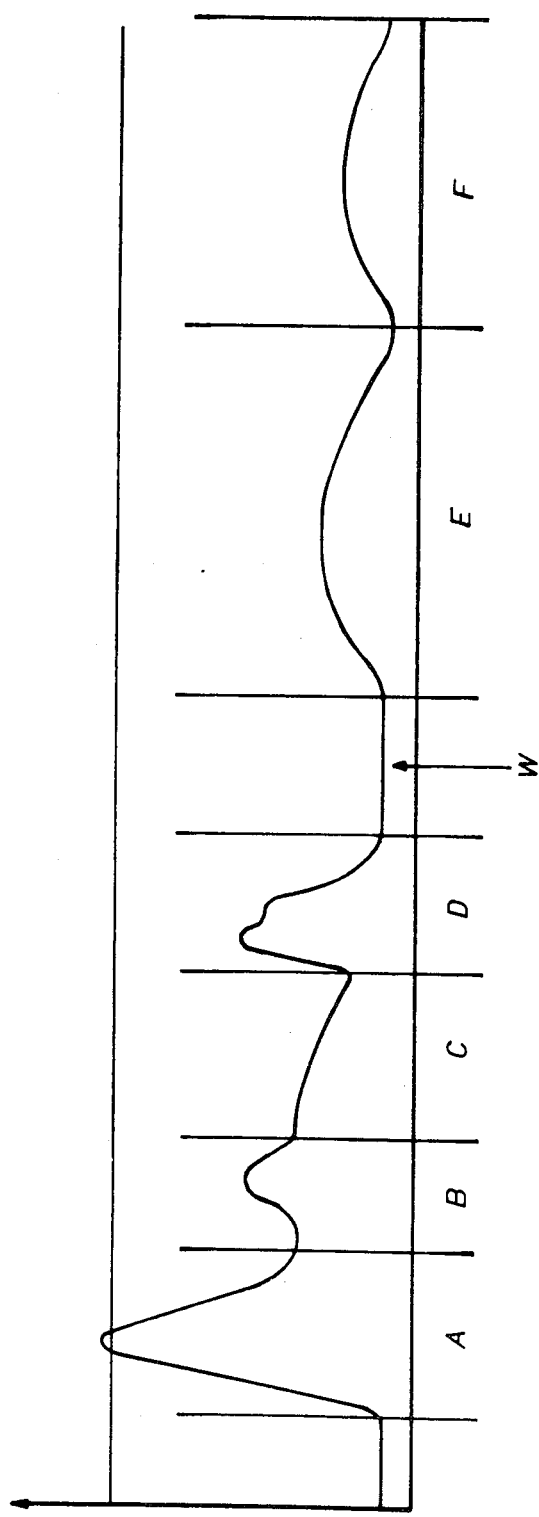
Figure 8:
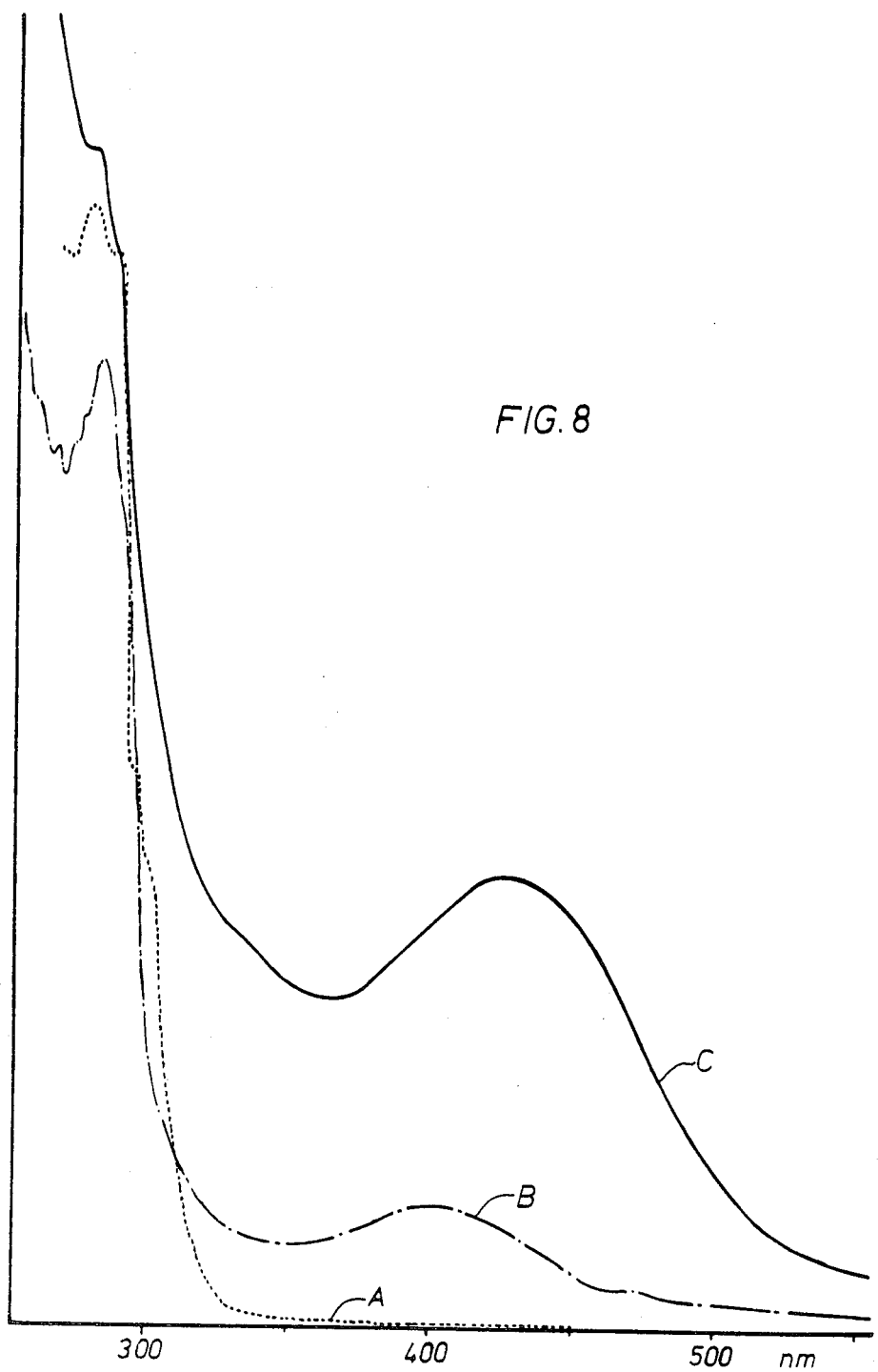

FIG. 6 shows the percentage inhibition of 0.25 nkat of granulocyte elastase (human) by some azo-BPTI derivatives according to the invention (determined by the method of J. Bieth et al.) with a 15 minute pre-incubation of the inhibitor and the enzyme (compare also Table 6).

Table 3

Percentage inhibition[1] of 1.1 nkat of pancrease elastase (pig) by various azo-BPTI derivatives using elastin-Congo Red as the substrate, determined by the method of M.A. Naughton and F. Sanger [Biochem. J. 78, 156 (1961)] with a 15 minute pre-incubation (+) and without (−) pre-incubation of the enzyme and the inhibitor.

| Axo-derivative prepared according to Example | % inhibition by μg of preparation | | | | | | | | | |
|---|---|---|---|---|---|---|---|---|---|---|
| | 50 | | 25 | | 12.5 | | 5 | | 2.5 | |
| | + | − | + | − | + | − | + | − | + | − |
| 5 | 96 | 87 | 77 | 70 | 55 | 51 | 42 | 29 | 30 | 19 |
| 7 | 77 | 89 | 56 | 73 | 35 | 41 | 24 | 25 | 7 | 17 |
| 9 | 75 | 89 | 60 | 71 | 45 | 62 | 31 | 29 | 19 | 16 |
| 11 | 92 | 92 | 87 | 76 | 62 | 56 | 31 | 33 | 17 | 12 |
| 17 | 69 | 84 | 58 | 75 | 38 | 48 | 35 | 27 | 21 | 16 |
| 19 | 79 | 87 | 55 | 75 | 46 | 46 | 35 | 25 | 20 | 10 |
| 27 | — | — | 89 | 82 | 42 | 39 | 28 | 20 | — | — |
| 28 | — | — | 91 | 82 | 54 | 43 | — | — | — | — |
| 36 | — | — | 76 | 76 | 38 | 26 | — | — | — | — |
| 38 | 73 | 75 | 63 | 53 | 51 | 34 | 34 | 20 | 22 | 10 |
| 41 | — | — | 82 | 98 | 35 | 41 | — | — | — | — |
| 42 | — | — | 85 | 90 | 60 | 72 | 35 | 41 | 22 | 25 |

[1]Calculated from: % inhibition = $\left(1 - \dfrac{\Delta \text{OD Test}}{\Delta \text{OD Enzyme control}}\right) \cdot 100$

Table 4

Percentage inhibition[1] of 0.25 nkat of pancreas elastase (pig) by various azo-BPTI derivatives using soluble elastin as the substrate, by the method of S. Keller and I. Mandl [Biochem. Med. 5, 342 (1971)] with a 15 minute (+) pre-incubation and without pre-incubation (−) of the enzyme and the inhibitor.

| Azo-BPTI derivative prepared according to Example | % inhibition by μg of preparation | | | | | | | | | |
|---|---|---|---|---|---|---|---|---|---|---|
| | 50 | | 25 | | 12.5 | | 5 | | 2.5 | |
| | + | − | + | − | + | − | + | − | + | − |
| 1 | 51 | 46 | 54 | 45 | 46 | 29 | 14 | 14 | 3 | 3 |
| 2 | 61 | 54 | 47 | 53 | 28 | 32 | — | — | — | — |
| 3 | 86 | 75 | 82 | 74 | 68 | 73 | 37 | 32 | 22 | 16 |
| 4 | 74 | 67 | 65 | 62 | 55 | 58 | 32 | 40 | 19 | 23 |
| 5 | 86 | 84 | 82 | 83 | 78 | 77 | 63 | 56 | 37 | 40 |
| 6 | 55 | 54 | 23 | 47 | 19 | 22 | — | — | — | — |
| 7 | 87 | 83 | 83 | 80 | 55 | 66 | 36 | 48 | 20 | 28 |
| 9 | 95 | 87 | 73 | 68 | 47 | 48 | 28 | 39 | 10 | 23 |
| 11 | 89 | 74 | 83 | 72 | 68 | 72 | 52 | 63 | 33 | 29 |
| 17 | 94 | 87 | 93 | 92 | 82 | 75 | 45 | 46 | 30 | 18 |
| 18 | 87 | 68 | 73 | 53 | 60 | 48 | 31 | 25 | 15 | 10 |
| 19 | 91 | 79 | 79 | 72 | 73 | 67 | 59 | 40 | 32 | 15 |
| 27 | — | — | 94 | 92 | 67 | 78 | 56 | 35 | 27 | 17 |

| Azo-BPTI derivative prepared according to Example | % inhibition by μg of formulation | | | | | | | | | |
|---|---|---|---|---|---|---|---|---|---|---|
| | 50 | | 25 | | 12.5 | | 5 | | 2.5 | |
| | + | − | + | − | + | − | + | − | + | − |
| 28 | — | — | 99 | 99 | 97 | 98 | 85 | 83 | 82+ | 83+ |
| 36 | — | — | 99 | 99 | 87 | 84 | 48 | 50 | 23 | 30 |
| 38 | 92 | 91 | 91 | 93 | 61 | 86 | 41 | 49 | 26 | 28 |
| 42 | 71 | 71 | 35 | 32 | 18 | 15 | — | — | — | — |

[1] Calculated from: % inhibition $= \left(1 - \frac{\Delta \text{OD Test}}{\Delta \text{OD Enzyme control}}\right) \cdot 100$ (+) 1 μg: 47 and 51% inhibition respectively

Table 5

Percentage inhibition [1] of a 0.25 nkat of pancreas elastase (pig) by various azo-BPTI derivatives using succinyl-L-alanyl-L-alanyl-L-alanine-p-nitroanilide, by the method of J. Bieth et al. [Biochem. Med. 11, 350 (1974) with a 15 minute (+) pre incubation and without (−) pre-incubation.

| Azo-BPTI derivative prepared according to Example | % inhibition by μg of preparation | | | | | | | | | |
|---|---|---|---|---|---|---|---|---|---|---|
| | 50 | | 25 | | 12.5 | | 5 | | 2.5 | |
| | + | − | + | − | + | − | + | − | + | − |
| 1 | 83 | 89 | 58 | 65 | 31 | 37 | 16 | 18 | 12 | 5 |
| 3 | 81 | 85 | 52 | 61 | 26 | 34 | 19 | 10 | — | — |
| 4 | 90 | 89 | 58 | 65 | 38 | 51 | 18 | 21 | 5 | 13 |
| 5 | 86 | 81 | 84 | 62 | 44 | 35 | 24 | 14 | — | — |
| 7 | 97 | 89 | 89 | 63 | 55 | 40 | 36 | 22 | 20 | 12 |
| 9 | — | — | 92 | 90 | 71 | 66 | 40 | 34 | 18 | 14 |
| 10 | 97 | 97 | 86 | 91 | 59 | 67 | 23 | 31 | 10 | 17 |
| 17 | — | — | 94 | 92 | 82 | 73 | 56 | 46 | 41 | 22 |
| 26 | — | — | 82 | 78 | 56 | 52 | 41 | 34 | 30 | 20 |
| 27 | — | — | 96 | 98 | 86 | 92 | 77 | 76 | 43 | 33 |
| 28 | — | — | 100 | 100 | 100 | 100 | 68 | 60 | 38 | 32 |
| 35 | — | — | 90 | 87 | 65 | 64 | 37 | 31 | 21 | 15 |
| 38 | — | — | 94 | 92 | 82 | 73 | 56 | 46 | 41 | 22 |
| 39 | — | — | 92 | 94 | 71 | 68 | 47 | 34 | 29 | 15 |
| 40 | — | — | 92 | 89 | 78 | 75 | 45 | 40 | 26 | 16 |
| 41 | — | — | 96 | 93 | 77 | 73 | 42 | 30 | 22 | 17 |
| 46 | — | — | 77 | 66 | 38 | 32 | — | — | — | — |

[1] Calculated from: % inhibition $= \left(1 - \frac{\Delta \text{OD Test}}{\Delta \text{OD Enzyme control}}\right) \cdot 100$

Table 6

Percentage inhibition[1] of 0.25 nkat of granulocytes elastase (human) by various azo-BPTI derivatives using succinyl-L-alanyl-L-alanyl-L-alanine-p-nitroanilide as the substrate, determined by the method of J. Bieth et al. [Biochem.Med. 11, 350 (1974)] with a 15 minute (+) pre-incubation and without (−) pre-incubation of the enzyme and inhibitor.

| Azo-BPTI derivative prepared according to Example | % inhibition by μg of preparation ||||||||
|---|---|---|---|---|---|---|---|---|
| | 50 || 25 || 12.5 || 5 ||
| | + | − | + | − | + | − | + | − |
| 3  | 55 | 56 | 36 | 36 | 24 | 23 | 10 | 11 |
| 4  | 60 | 69 | 45 | 41 | 23 | 23 | 9  | 15 |
| 5  | 78 | 75 | 56 | 52 | 31 | 30 | 13 | 15 |
| 7  | 35 | 32 | 20 | 19 | 0  | 0  | 0  | 0  |
| 11 | 48 | 52 | 35 | 36 | 24 | 23 | 9  | 15 |
| 17 | 70 | 47 | 45 | 39 | 29 | 31 | 15 | 15 |
| 19 | 60 | 67 | 40 | 42 | 25 | 23 | 12 | 11 |
| 27 | 81 | 65 | 54 | 42 | 36 | 36 | 19 | 15 |
| 28 | 96 | 60 | 93 | 33 | 91 | 24 | —  | —  |
| 35 | 81 | 73 | 60 | 51 | 42 | —  | —  | —  |
| 36 | 78 | 79 | 59 | 66 | 34 | 36 | 16 | 19 |
| 46 | 85 | 85 | 52 | 52 | 32 | 30 | —  | —  |
| 47 | 62 | 61 | 52 | 51 | 37 | 37 | 18 | 15 |
| 51 | 79 | 80 | 54 | 54 | 29 | 31 | —  | —  |

[1]Calculated from: % inhibition = $\left(1 - \frac{\Delta \text{ OD Test}}{\Delta \text{ OD Enzyme Control}}\right) \cdot 100$ (b) Inhibition of chymotrypsin and chymotrypsin-like enzymes (d) Pancreas chymotrypsin inhibition The activity of chymotrypsin was determined by means of fluorescence spectrophotometry by the method of H. Rinder-knecht and R. M. Fleming [Clinica Chim. Acta 59, 135 (1975)] using a Leitz PM-Q II spectrophotometer. The concentration in the test of glutaryl-diglycyl-L-phenylalanin)-β-naphthyl amid (obtained from Messrs. Bachem, Liestal, Switzerland), used as the substrate, was $6.3 \times 10^{-4}$ M; 900 ng of α-chymotrypsin (crystalline formulation from Novo Industri A.S.) were employed per 3 ml of test solution. Light of the wavelength $\lambda_{ex}=365$ nm was used to excite the fluorescent substance and the measurements were carried out at $\lambda_{em}=415$ nm. The enzyme solution and the solution of the azo-BPTI derivative were pre-incubated for 15 minutes at 25° C. for the determination of the inhibition values and the increase in fluorescence after adding the substrate was recorded for 15 minutes.

The percentage inhibition was calculated by extrapolating the 15 minute fluorescence values from the region of linear increase, before the fall-off due to lack of substrate, from $$\left(1 - \frac{\Delta_F \text{Test}}{\Delta_F \text{Enzyme control}}\right) \cdot 100$$

The inhibition values listed in Table 7 for some azo-BPTI derivatives (expressed in %) are relative to the inhibition effected by the same amount of BPTI (=100%).

β Cathepsin G inhibition

The activity of cathepsin G was determined photometrically, using benzoyl-L-tyrosine ethyl ester, by the method of B. C. W. Hummel [Canad. J. Biochem. Physiol. 37, 1393 (1959)] in the version of K. N. Rao and B. Lombardi [Anal. Biochem. 65, 548 (1975)]. 20 nkat of enzyme per test were pre-incubated with the inhititors for 15 minutes; after adding the substrate, the increase in the extinction at 256 nm was then recorded for 5 minutes. The percentage inhibitions were calculated, after extrapolating from the linear region of the increase, from $$\% \text{ inhibition} = \left(1 - \frac{OD_{Test}}{OD \text{ Enzyme control}}\right) \cdot 100$$

(c) Kininogenase inhibition (a) Plasma kininogenase inhibition

The kininogenase activity was determined by the pH-stat method, according to C. Sampaio, S. C. Wong and E. Shaw [Arch. Biochem. Biophys. 165, 133 (1974)], but, because of the higher rate of hydrolysis, benzoyl-L-arginine ethyl ester hydrochloride was used as the substrate in place of tosyl-L-arginine methyl ester hydrochloride. The mixture of the isoenzymes was isolated by affinity chromatography from the human plasma fraction Cohn IV-1, by the method of C. Sampaio et al. [Arch. Biochem. Biophys. 165, 133 (1974)]. The inhibition values listed in Table 7 for some azo-BPTI derivatives were determined as indicated under chymotrypsin inhibition.

Table 7

Inhibition of serine proteases by various azo-BPTI derivatives, compared with the inhibitions effected by the same amounts of BPTI (100%)

| Designation of the substance | Chymotrypsin | Kinogenase ||  Plasmin | Trypsin |
|---|---|---|---|---|---|
| | | Pancrease | Plasma | | |
| BPTI (comparison) | 100 | 100 | 100 | 100 | 100 |
| Azo-BPTI derivative according to Example 1 | 113 | 108 | 86  | 49 | 94  |
| 3  | 75  | 94  | 81  | 70 | 55  |
| 4  | 105 | 90  | 102 | 85 | 60  |
| 5  | 118 | 84  | 92  | 64 | 88  |
| 7  | 95  | 94  | 123 | 60 | 88  |
| 9  | 93  | 73  | 88  | 49 | 56  |
| 10 | 67  | 102 | 112 | 36 | 57  |
| 17 | 103 | 97  | 129 | 40 | 35  |
| 18 | 115 | 101 | 105 | 81 | 89  |
| 19 | 100 | 93  | 105 | 43 | 100 |
| 20 | 95  | 89  | 92  | 42 | 50  |
| 23 | 100 | 91  | 100 | 55 | 87  |
| 26 | 33  | 29  | 92  | 15 | 19  |
| 35 | 113 | 97  | 94  | 66 | 78  |
| 38 | 98  | 84  | 53  | 38 | 50  |

Table 7-continued
Inhibition of serine proteases by various azo-BPTI derivatives, compared with the inhibitions effected by the same amounts of BPTI (100%)

| Designation of the substance | Chymotrypsin | Kinogenase Pancrease | Kinogenase Plasma | Plasmin | Trypsin |
|---|---|---|---|---|---|
| 46 | 74 | 97 | 96 | 90 | 64 |
| 47 | 98 | 63 | 71 | 42 | 100 |
| 51 | 100 | 95 | 79 | 90 | 100 |

(β) Pancreas kininogenase inhibitors

The test enzyme was obtained by the method of C. Kutzbach and G. Schmidt-Kastner [Z. Physiol. Chem. 353, 1099 (1972)] and the activity determinations were carried out by the method of the same authors (see above). The inhibition values listed in Table 7 for some azo-BPTI derivatives were determined as indicated under chymotrypsin inhibition.

(d) Plasmin inhibition

The enzymatic activity of plasmin was determined using azocasein. Plasminogen which was activated with urokinase and had been isolated from human plasma by means of affinity chromatography [D. G. Deutsch and E. T. Merz; J. Med. 3, 224 (1972)] was used as the enzyme.

The preparation of the substrate and the principle of the test are described in P. M. Starkey and A. J. Barrett [Biochem. J. 155, 255 (1976)]. For each determination, two batches A and B, each containing 0.6 CU of plasmin, dissolved in 1.0 ml of a buffer (0.1 M tris-(hydroxymethyl)-aminomethane and 0.05 M NaCl, adjusted to pH 7.2 with HCl), are prepared. In each case 1.25 μg of BPTI or BPTI derivatives, dissolved in 1.25 ml of buffer (see above) are added to both batches; one batch each of A and B with 1.25 ml of buffer instead of the inhibitor are used for comparison. All the batches are incubated for 10 minutes at 37° C. and 0.45 ml of a 2% azocasein solution (in buffer, see above) is then added to each. 0.3 ml of a 30% trichloracetic acid solution (TCA) is then added directly to series A; series B is incubated for 60 minutes at 37° C. and 0.3 ml of TCA is then added. The batches are centrifuged after about 20 minutes; the extinctions of the supernatants are determined photometrically at 340 nm in a 1 cm cell.

The difference in the extinctions of the parallel batches A and B ($\Delta E$) is considered to be a measure of the enzymatic activity.

If the difference in extinction which is caused by plasmin on its own is designated $\Delta E_{100}$ and the difference in extinction measured in the presence of inhibitors is designated $\Delta E$, the inhibition of the plasmin by the inhibitors, under the conditions indicated, is given by the following expression $$\left(1 - \frac{OD\ Test}{OD\ Enzyme\ control}\right) \cdot 100$$

The inhibition values (expressed in %) listed in Table 7 for some azo-BPTI derivatives are relative to the inhibition effected by the same amount of BPTI (=100%).

(e) Trypsin inhibition

The determination of trypsin was carried out, using benzoyl-L-arginine ethyl ester hydrochloride as the substrate, by the pH-stat method according to R. Ruyssen (Symposium on Pharmaceutical Enzymes and their Assay, Universitaire Pers. Ghent, Belgium 1969, page 110). The inhibition values given in Table 7 for some azo-BPTI derivatives were determined as indicated under chymotrypsin inhibition. Test arrangement for determining the anti-inflammatory action in rats (a) Kaolin-induced inflammatory reaction The inflammatory reaction was induced by intraplantary injection of 0.1 ml of a 10% kaolin suspension (Bolus white, finely powdered, Merch AG, Darmstadt) in a back paw of Wistar rats weighing 130–160 g. The azo-BPTI derivatives according to the invention and also BPTI, which were used for the treatment of the inflammatory reaction, were dissolved in a 0.9% sodium chloride solution in a concentration of 10–20 mg/ml. The test animals were treated by intraperitoneal, intramuscular, subcutaneous or intravenous injection of 0.5–1.0 ml of a solution of azo-BPTI derivatives and, for comparison, of BPTI, either prophylactically, that is to say before setting of the inflammation noxa, or therapeutically, that is to say after setting of the inflammation noxa. The swelling of the inflamed paw, which is a measure of the severity of the inflammatory reaction, was followed, as a function of time, using the KEMPER antiphlogmeter (F. Kemper and G. Ameln, Z. ges. exp. Med. 131, 407–411 (1959)).

The value measured 4 hours after setting of the inflammation noxa was used to determine the relationship between the dose and the effect. The result of the comparison of various azo-BPTI derivatives with BPTI is given in Table 8. The doses, in mg/kg, which effect a 50% ($ED_{50}$) and 75% ($ED_{75}$) inhibition of the swelling of the paw, compared with the untreated control group, are given.

The comparison, in Table 8, of the action of the azo-BPTI derivatives according to the examples shows that they are superior to BPTI in respect to their anti-inflammatory action.

Table 8:

Inhibition of the kaolin-induced inflammatory reaction in a rat's paw by intravenous treatment with BPTI and azo-BPTI derivatives. The treatment was carried out 15 minutes after setting of the inflammation noxa. The average values and the 5% confidence range are recorded. In each dosegroup and also for the controls 5 animals were used.

| Designation of the substance | obtained according to Example | $ED_{50}$ mg/kg | $ED_{75}$ mg/kg |
|---|---|---|---|
| BPTI | — | 33.9 (26.7–52.1) | not achievable |
| Azo-BPTI derivative | 1 | 11.7 24.4)13.3) | 27.3 (23.4–50.0) |
| Azo-BPTI derivative | 2 | 9.8 ( 8.9–10.5) | 26.8 (24.0–29.3) |
| Azo-BPTI derivative | 3 | 6.5 (5.4–7.6) | 17.4 (15.0–20.8) |
| Azo-BPTI derivative | 6 | 8.7 (7.6–9.8) | 25.9 (21.5–34.5) |

Table 8:-continued

Inhibition of the kaolin-induced inflammatory reaction in a rat's paw by intravenous treatment with BPTI and azo-BPTI derivatives. The treatment was carried out 15 minutes after setting of the inflammation noxa. The average values and the 5% confidence range are recorded. In each dosegroup and also for the controls 5 animals were used.

| Designation of the substance | obtained according to Example | $ED_{50}$ mg/kg | $ED_{75}$ mg/kg |
|---|---|---|---|
| Azo-BPTI derivative | 9 | 9.8 (8.5–10.4) | 15.6 (13.7–17.6) |
| Azo-BPTI derivative | 10 | 1.8 (1.4–2.2) | 3.4 (2.8–4.3) |
| Azo-BPTI derivative | 17 | 5.4 (5.0–5.9) | 8.8 (8.0–9.9) |
| Azo-BPTI derivative | 19 | 7.8 (6.1–9.6) | 19.5 (16.3–24.1) |
| Azo-BPTI derivative | 37 | 10.4 (10.1–11.1) | 15.9 (15.1–16.9) |
| Azo-BPTI derivative | 38 | 5.7 (3.8–7.2) | 12.4 (9.8–15.6) |
| Azo-BPTI derivative | 44 | 9.1 (7.8–10.4) | 20.2 (16.9–25.4) |
| Azo-BPTI derivative | 47 | 1.5 (1.1–2.1) | 4.5 (3.1–7.4) |
| Azo-BPTI derivative | 48 | 9.9 (8.7–11.3) | 22.1 (18.2–28.7) |
| Azo-BPTI derivative | 49 | 2.7 (2.3–3.1) | 6.4 (5.6–7.4) |
| Azo-BPTI derivative | 51 | 3.5 (2.1–4.8) | 14.3 (11.7–18.2) |
| Azo-BPTI derivative | 52 | 4.5 (2.9–5.9) | 15.6 (13.0–20.2) |
| Azo-BPTI derivative | 55 | 10.5 (9.8–11.7) | 20.8 (18.5–24.4) |

(b) Aerosil induced inflammatory reaction

The inflammatory reaction was induced by intraplantary injection of 0.1 ml of a 2% aerosil suspension (Aerosil 200, Degussa AG, Frankfurt) in a back paw of Wistar rats weighing 130–160 g. The azo-BPTI derivatives according to the invention and the BPTI, used for the treatment of the inflammatory reaction, were dissolved in a 0.9% sodium chloride solution in a concentration of 10–20 mg/ml. The test animals were treated by intraperitoneal, subcutaneous or intravenous injection of 0.5–1.0 ml of a solution of azo-BPTI derivatives and, for comparison, of BPTI 15 hours after setting of the inflammation noxa. The swelling of the inflamed paw, which is a measure of the severity of the inflammatory reaction, was followed, as a function of time, using the KEMPER antiphlogmeter. In order to ascertain the relationship between the dose and the effect, the value obtained 21 hours after the induction of inflammation (=6 hours after injection of the azo-BPTI derivatives according to the invention or of BPTI) was determined. The result of the comparison of the various azo-BPTI derivatives with BPTI is given in Table 9. The doses, in mg/kg, which effect a 30% ($ED_{30}$) and 50% ($ED_{50}$) inhibition of the swelling of the paw, compared with the untreated control groups, are given.

The result, in Table 9, of the therapy tests with the azo-BPTI derivatives according to the examples shows the activity, of the azo-BPTI derivatives used, in this experimental model in which BPTI in the same dosage does not inhibit the inflammatory reaction. The superiority of the azo-BPTI derivatives as medicaments, compared with BPTI, is thus demonstrated.

Table 9:

Inhibition of the aerosil-induced inflammatory reaction in rat's paw by intravenous treatment with BPTI and BPTI derivatives. The treatment was carried out 15 hours after setting of the inflammation noxa. The average values and the 5% confidence range are recorded. 5 animals were used per dosegroup and 5 for the controls for each derivative tested.

| Designation of the substance | obtained according to Examnple | $ED_{30}$ mg/kg | $ED_{50}$ mg/kg |
|---|---|---|---|
| BPTI | — | NO ACTIVITY | |
| Azo-BPTI derivative | 10 | 7.8 (5.5–13.3) | — |
| Azo-BPTI derivative | 18 | 5.7 (4.6–7.8) | 24.7 (15.6–51.0) |
| Azo-BPTI derivative | 19 | 10.3 (6.6–14.1) | — |
| Azo-BPTI derivative | 47 | 3.0 (2.7–3.4) | 5.6 (4.9–6.5) |
| Azo-BPTI derivative | 49 | 3.6 (3.3–4.0) | 6.5 (5.9–7.5) |
| Azo-BPTI derivative | 50 | 1.1 (.26–2.1) | 5.6 (3.5–7.2) |

The azo-BPTI derivatives according to the invention as medicaments are superior to BPTI. Their inhibitory actions on the elastases from the pancreas and granulocytes are of particular advantage and open up new possibilities for therapeutic use. An important role is played by pancreas elastase in pancreatitis [M. C. Geokas, H. Rinderknecht, V. Swanson, B. P. Vitron and B. J. Haverback, Clin. Res. 16, 285 (1968)]; by serum elastase in arteriosclerosis [U. Butturini and M. Langen, Klin. Wochenschr. 40, 472 (1962)] and by granulocyte elastase in acute and chronic inflammations with damage to the connective tissue [A. Janoff, Amer. J. Pathol. 68, 579 (1972)], in damage to the vascular walls [A. Janoff and J. D. Zeligs, Science 161, 702 (1968)] and also in necrotising diseases and degeneration of lung tissue, for example in the case of emphysema [G. M. Turino, R. M. Senior, B. D. Garg, S. Keller, M. M. Levi and I. Mandl, Science 165, 709 (1969); H. E. Evans, M. M. Levi and I. Mandl, Amer. Rev. Respir. Dis. 101, 359 (1970) as well as A. Janoff, R. A. Sandhaus, V. D. Hospelhorn and R. Rosenberg, Proc. Soc. Exptl. Biol. Med. 140, 516 (1972)]. The role of lysosomal enzymes and in particular of granulocyte elastase in inflammatory reactions which have an immunological cause [M. Koono, M. Muto and H. Hayashi, Tohoku J. Explt. Med. 94, 231 (1968)], for example in rheumatoid arthritis [G. Weissmann and J. Spilberg, Arthritis Rheumat. 11, 162 (1968)] is equally important.

It has been found that in models for an acute inflammatory reaction the azo-BPTI derivatives according to the invention are superior to BPTI since, when the derivatives are used, not only is the same action as with BPTI achieved with distinctly smaller dosages but the inflammatory reaction is significantly inhibited even when the derivatives are administered several hours after setting of the inflammation noxa. A therapeutic action of this type cannot be achieved with BPTI on a single administration in a kaolin and aerosil model.

This changed action and effectiveness, compared with BPTI, of the azo-BPTI derivatives according to the invention can be attributed to the changed inhibition spectrum and other changed properties, such as a greater retention time and time of action in the body of the test animals. The BPTI derivatives according to the invention are therefore biologically to be clearly differentiated from BPTI.

Because of their biological activity, the new azo-BPTI derivatives, according to the invention can be employed, in particular, for the treatment of the following diseases and disease symptoms:

1. Various forms of shock and post-traumatic and post-operative complications.
2. disorders in blood clotting,
3. acute and chronic inflammatory reactions, especially for the therapy and prophylaxis of damage to organs, such as, for example, pancreatitis and radition-induced enteritis,
4. inflammatory reactions caused by immune complexes, such as immune-vasculitis, glomerulonephritis and arthritides,
5. collagenoses, especially rheumatoid arthritis,
6. arthritides caused by deposits due to metabolic processes (for example gout) and
7. degeneration of the elastic components of the connective tissue or organs, such as in the case of arteriosclerosis and pulmonary emphysema.

The new active compounds can be converted into the customary formulations suitable for administration to human or non-human animals analogously to BPTI.

The present invention therefore provides a pharmaceutical composition containing as active ingredient a compound of the invention in admixture with a solid or liquefied gaseous diluent, or in admixture with a liquid diluent.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents.

The pharmaceutical compositions according to the invention preferably contain about 0.1 to 99.5, more preferably from about 0.5 to 95% of the active ingredient by weight of the total composition. Solutions or suspensions usually contain from 0.01 to 100 mg/ml of solution, preferably from 0.1 to 10 mg/ml.

In addition to a compound of the invention, the pharmaceutical compositions and medicaments according to the invention can also contain other pharmaceutically active compounds and/or a plurality of compounds of the invention. For example, the resulting compositions may include a combination of different inhibitory substances which have mutually complementary spectra of action.

The discrete coherent portions constituting the medicament according to the invention will generally be adapted, by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 5 mg to 4 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally or intravenously), rectally or locally.

The following methods of administration may be mentioned as being preferred:
1. parenteral, intravenous, intramuscular, subcutaneous, intraarticular and intratumoral,
2. local; as an aerosol and
3. oral, appropriately in application forms which are resistant to gastric juice and/or soluble in the small intestine.

In general it has proved advantageous to administer amounts of from about 0.1 mg to about 40 mg, preferably about 1 to to about 25 mg/kg of body weight per day to achieve effective results. Nevertheless, it can at times be necessary to deviate from these dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst in other cases the upper limit mentioned must be exceeded to achieve the desired results. Where large amounts are administered it can be advisable to divide these into several individual administrations over the course of the day.

The following Examples illustrate the invention.

EXAMPLE 1

60 mg of aniline oxalate (330 $\mu$ moles) were dissolved in 5 ml of N hydrochloric acid and a solution of 25 mg of sodium nitrite (362 $\mu$ mols) in 0.2 ml of water was stirred into the mixture at 4°. After 10 minutes, approximately 10 mg of urea were added to the reaction solution and it was combined, after a further 5 minutes, with a solution of 1 g of BPTI (154 $\mu$ moles) in 10 ml of water, which had been precooled to 4°. The pH value of the reaction mixture was adjusted with 4 N sodium hydroxide solution to 9.0, whilst cooling and stirring vigorously, and the suspension was stirred for a further 20 minutes whilst cooling. After adding a small quantity of phenol, the mixture was acidified with acetic acid and the clear solution was filtered through Sephadex G 10 using 0.1 M acetic acid as the eluting agent, in order to remove the salts. After Lyophiliation of the protein containing eluates the substance was chromatographed on Sephadex G 50 using 0.1 M acetic acid as the eluting agent in order to remove the higher-molecular weight fractions (10 mg=1%).

720 mg of an orange-yellow substance (72%) were isolated as the lyophilisate.

EXAMPLE 2

A solution of 69 mg of sodium nitrite (1 mmol) in 0.2 ml of water was added at 4°, whilst stirring well, to a solution of 129 mg of p-methylaniline hydrochloride (900 $\mu$ mols) in 5 ml of 2 N hydrochloric acid. After 15 minutes, a small quantity of amidosulphonic acid was added to the reaction solution, followed by a cooled solution of 1 g of BPTI (154 $\mu$ mols) in 10 ml of water and the quantity of 4 M sodium hydroxide solution required to adjust the pH value of the reaction mixture to 9. The resulting red suspension was stirred for 15 minutes at 4°, a precipitate being deposited. A small quantity of phenol was now introduced into the suspension and, after 5 minutes, acetic acid was introduced until a pH of 4.5 was reached. The solution, which was now clear, was freed from salts by filtration through Sephadex G 10, using 0.1 M acetic acid as the eluting agent. After freeze-drying the eluates containing protein, 52 mg (5.5%) of higher molecular weight fractions were separated off by chromatograhy on Sephadex G 50, using 0.1 M acetic acid as the eluting agent. 670 mg (67%) of a yellow substance were isolated by freeze-drying the main fraction.

EXAMPLE 3

A solution of 125 mg of sodium nitrite (1.81 mmols) in 0.5 ml of water was stirred at 4° into a solution of 192 mg of p-methoxyaniline (1.54 mmols) in 20 ml of 1 N hydrochloric acid. After 15 minutes a small quantity of urea was added to the reaction solution and, after a further 15 minutes, it was combined with a pre-cooled solution of 5 g of BPTI (770 $\mu$ mols) in 30 ml of water and 4 N sodium hydroxide solution was added until the pH value of the reaction mixture was 9.0. After stirring for 15 minutes whilst cooling with ice, a small quantity of phenol was added to the reaction mixture, in which a precipitate had formed. After a further 5 minutes the reaction mixture was acidified with glacial acetic acid, whereupon the precipitate dissolved. The reaction mixture was filtered through Sephadex G 10 (5×100 cm) usng 0.2 M acetic acid as the eluting agent, in order to remove the salts; the fractions containing protein wre lyophilised. The lyophilisate as fractionated on Sephadex G 50 using 0.1 M acetic acid as the eluting agent. A higher-molecular weight fraction (0.19 g=4% after lyophilisation) and the yellow monomeric reaction product (4.19 g=84% after lyophilisation) were thus isolated.

EXAMPLE 4

25 mg of solid sodium nitrite (362 $\mu$ mols) were added at 4°, whilst stirring well, to a solution of 42.5 mg of p-aminobenzoic acid (310 $\mu$ mols) in 5 ml of N hydrochloric acid. After 10 minutes a small quantity of amidosulphonic acid as added to the reaction solution, which, after a further 5 minutes, was combined with a solution of 1 g of BPTI (154 $\mu$ mols) in 10 ml of water. 4 N sodium hydroxide solution was now added to the reaction mixture until a pH of 8.8 was reached and the mixture was stirred for 20 minutes whilst cooling with ice. After adding a small quantity of phenol, glacial acetic acid was added to the reaction mixture, after a further 5 minutes, until there was a distinctly acid reaction and the mixture was freed from salts by filtration through Sephadex G 10 using 0.1 M acetic acid as the eluting agent. The compounds of higher molecular eight - 80 mg (8%) - were separated off by chromatography on Sephadex G 50. After freeze-drying the main fraction, 760 mg of a yellow-orange substance (76%) were obtained.

EXAMPLE 5

25 mg of solid sodium nitrite (362 $\mu$ mols) were added, whilst stirring well, to a solution of 54 mg of p-sulphanilic acid (310 $\mu$ mols) in 5 ml of N hydrochloric acid. The mixture was stirred for 10 minutes whilst cooling with ice and a small quantity of urea was then added to the reaction mixture, followed, after a further 5 minutes, by sodium hydroxide solution until a pH value of 6.5 had been reached. The solution of the diazonium salt was then combined with a cooled solution of 1 g of BPTI (154 $\mu$ mols) in 10 ml of 1 M potassium carbonate/sodium carbonate buffer, pH 9.4. The reaction solution was stirred for 10 minutes at 4° and a small quantity of phenol was then added to it. The pH was then adjusted to a value of 5.5 by adding acetic acid dropwise and the mixture was filtered through Sephadex G 10, using 0.1 M acetic acid as the eluting agent (column: 2.2×90 cm), in order to remove the salts. After the orange fraction containing protein had been freeze-dried, the polymeric fractions were separated off by chromatography on Sephadex G 50. 150 mg of a polymer fraction (15%) and 600 mg of a monomeric orange-coloured substance (60% yield) were obtained.

EXAMPLE 6

25 mg of sodium nitrite (362 μ mols) were added at 4° to a solution of 52 mg of p-arsanilic acid (308 μ mols) in 5 ml of N hydrochloric acid, whilst stirring well. After 15 minutes a small quantity of amidosulphonic acid was introduced into the reaction solution and the latter was combined, after a further 5 minutes, with a cooled solution of 1 g of BPTI (154 μ mols) in 10 ml of water. The pH was adjusted to a value of 8.8 by adding sodium hydroxide solution and the reaction solution was stirred for 15 minutes whilst cooling with ice. A small quantity of phenol was then added to the mixture and, after a further 5 minutes, glacial acetic acid was added until pH 5.0 was reached. The reaction solution was now freed from salts by filtration throgh Sephadex G 10 - 2.2×120 cm - and higher-molecular weight fractions were separated of by chromatographing the desalted solution on Sephadex G 50 using 0.1 M acetic acid as the eluting solvent. After freeze-drying, 690 mg (69%) of a monomeric, orange-yellow substance were obtained, and in addition 90 mg (9%) of polymers.

EXAMPLE 7

320 mg of p-amino-o'-carboxydiphenyl ether hydrochloride (1.24 mmols), obtained by catalytic hydrogenation of p-nitro-o'-carboxydiphenyl ether [F. F. Blicke and D. F. Smith, J. Amer. Chem. Soc. 51, 1947 (1929)], were dissolved in 3 ml of absolute dimethylformamide and were precipitated in a finely divided form by adding a mixture of 5 ml of N hydrochloric acid and 0.2 ml of concentrated hydrochloric acid to the solution. After cooling the suspension to 4°, a solution of 95 mg of sodium nitrite (1.36 mmols) in 0.2 ml of water was added, whilst stirring well, and the reaction mixture was stirred for 20 minutes at 4°, a clear solution being formed immediately. After 20 minutes, approximately 50 mg of urea were added and the pH value of the reaction mixture was finally adjusted to 6.5 with 4 N sodium hydroxide solution. The reaction mixture was then combined with an ice-cold solution of 2 g of BPTI (308 μ mols) in 15 ml of a 1 M potassium bicarbonate/sodium carbonate buffer of pH 9.5. The reaction solution, in which a precipitate soon formed, was kept at 4° for 30 minutes, whilst stirring, and, finally, glacial acetic acid was added until pH 5.5 was reached. In order to remove the salts, the solution, which was now clear, was filtered through Sephadex G 10 using 0.1 acetic acid as the eluant (column: 120×2.3 cm). 140 mg (7%) of polymeric constituents were separated off by chromatography on Sephadex G 50 using 0.1 M acetic acid from the yellow substance obtained by freeze-drying the fraction containing protein. On freeze-drying, the main fraction gave 1 870 mg of a brown-orange substance (93%).

EXAMPLE 8

A solution of 107 mg of sodium nitrite (1.55 mmols) in 0.25 ml of water was added dropwise slowly at 4°, whilst stirring well, to a solution of 212 mg of p-aminodimethylaniline (1.55 mmols) in 2.5 ml of 4 N hydrochloric acid. After 5 minutes a small quantity of amidosulphonic acid was added to the dark reaction solution and, after a further 2 minutes, a solution, which had been pre-cooled to 4°, of 1 g of BPTI (154 μ mols) in 10 ml of water was added. 5 N sodium hydroxide solution was now added to the reaction mixture until pH 9.5 was reached and the olive-coloured solution was stirred for 10 minutes whilst cooling with ice. The pH value of the reaction mixture was then adjusted to 3.5 with glacial acetic acid and, in order to free the solution from salts, it was filtered through Sephadex G 10 using 0.1 M acetic acid as the eluting solvent. 72 mg of polymeric constituents (7%) were removed from the main refraction by chromatographing the eluates containing protein on Sephadex G 50 using acetic acid as the eluting agent. After freeze-drying, 783 mg of a brown substance (78%) remained.

EXAMPLE 9

After 62 mg of p-aminoacetophenone (462 μ mols) had been dissolved in 5 ml of 2 N hydrochloric acid, the diazonium salt thereof was prepared as described in Example 1. The pH of the diazonium salt solution as adjusted to a value of 4.0 with 4 N sodium hydroxide solution which had been cooled in ice, and the reaction mixture was then combined with a cooled solution of 1 g of BPTI in 10 ml of water. In order to achieve coupling, the reaction solution was stirred for 10 minutes at pH 8.8 in an ice bath. A precipitate immediately formed out with the formation of a red coloration. After a small quantity of phenol had been added, glacial acetic acid was added to the reaction mixture until a pH value of 4.5 was reached and the undissolved material was removed by centrifuging (10 minutes/3,000 r.p.m.). After desalting the supernatant solution over Sephadex G 10 and freeze-drying the eluates containing protein, 965 mg of an orange-coloured substance were obtained which was chromatographed on Sephadex G 50 using 0.1 M acetic acid as the eluting agent in order to remove higher-molecular constituents (97 mg; 10%). 876 mg (88%) of an orange-coloured substance were obtained by lyophilisation the main fraction.

EXAMPLE 10

100 mg of 3,5-dichloroaniline (615 μ mols) were dissolved in 0.5 ml of glacial acetic and were reprecipitated in a finely divided state by adding 5 ml of 2 N hydrochloric acid whilst stirring well. After this suspension has been cooled to 4°, a solution of 49 mg of sodium nitrite (710 μ mols) in 0.2 ml of water was stirred in, a clear solution being formed immediately. After stirring for 15 minutes, a small quantity of urea was added to this solution and it was combined, after a further 5 minutes, with a solution, pre-cooled to 4°, of 2 g of BPTI (308 μ mols) in 20 ml of water. The pH of the reaction mixture was now adjusted to a value of 8.6 with ice-cold, concentrated sodium hydroxide solution and the suspension which was immediately formed was stirred for 20 minutes whilst cooling with ice. A small quantity of phenol was then added to the reaction mixture and, after 3 minutes, acetic acid was added until a pH of 4.0 was reached. The solution was clarified by centrifuging and was then filtered through Sephadex G 10 using 0.1 M acetic acid as the eluting agent, in order to remove the salts, and the salt-free, freeze-dried substance was chromatographed on Sephadex G 50 using 0.1 M acetic acid. After lyophiliation 240 mg of substance (12%) were isolated in this way from the higher molecular weight fraction and 1,520 mg (76%) were isolated from the main fraction (orange-coloured).

EXAMPLE 11

187 mg of 3,5-dichloroaniline (1.15 mmols) were dissolved in 0.5 ml of glacial acetic acid and diazotised after precipitation with 10 ml of N hydrochloric acid, as described in Example 10. The diazonium salt solution was finally combined with a solution, pre-cooled to 4°, of 2.5 g of BPTI (385 $\mu$ mols) in 75 ml of 4.5 M urea solution and the pH of the reaction mixture was adjusted to a value of 10 with 4 N sodium hydroxide solution whilst stirring vigorously and cooling. After the reaction solution had been stirred at 4° C. for 45 minutes, a small quantity of phenol was added and, after a further 5 minutes, glacial acetic acid was added until a pH of 4.0 was reached. The solution was then concentrated to a volume of approximately 20 ml by ultra-filtration through a UM 2 filter and was freed from salts by filtration through Sephadex G 10 using 0.1 M acetic acid as the eluting agent. After the higher-molecular constituents had been separated off by chromatography on Sephadex G 50 using 0.1 M acetic acid as the eluting agent, 2 194 mg of an orange-coloured substance (88% of theory) were obtained by freeze-drying the main fraction.

EXAMPLE 12

186 mg of 3,5-dichloroaniline (1.15 mmols) were dissolved in a mixture of 0.5 ml of glacial acetic acid and 0.5 ml of propionic acid. 0.3 ml of concentrated sulphuric acid was added to this solution and approximately 0.3 ml of water was also added in order to dissolve the precipitated sulphate. After cooling to −15°, 175 mg of nitrosylsulphuric acid (1.38 mmols) were stirred into the mixture and it was kept at 0° to −5° C. for 20 minutes whilst stirring. 60 mg of urea (1 mmol) were then added to the reaction mixture which, after a further 20 minutes, was combined with a solution, pre-cooled to 4°, of 2.5 g of BPTI (385 $\mu$ mols) in 20 ml of water. Whilst stirring vigorously and cooling, the pH of the reaction solution was adjusted to a value of 4.0 with 4 N sodium hydroxide solution and was raised by 1 pH unit every 30 minutes. After a pH of 9.0 had been reached, a small quantity of phenol was added to the suspension and glacial acetic acid was then added until a pH of 4.0 was reached. The solution, which was now clear, was freed from salts by filtration through Sephadex G 10 using 0.1 M acetic acid as the eluting agent. Finally, high-molecular constituents were separated off by chromatography on Sephadex G 50. 2.15 g of an orange-coloured substance (86%) were obtained by freeze-drying the main fraction.

EXAMPLE 13

187 mg of 3,5-dichloroaniline (1.15 mmols) were dissolved by warming in 0.3 ml of a 1:1 mixture of acetic acid and propionic acid. After cooling to −10°, 190 mg of nitrosylsulphuric acid were added to the mixture and, finally 0.125 ml of concentrated sulphuric acid was added, whilst stirring well. An orange-coloured precipitate was formed immediately. After 15 minutes, 60 mg of urea were added to the mixture and, after adding 5 ml of dimethylsulphoxide, it was combined, after a further 20 minutes, with a solution of 1 g of BPTI in 10 ml of 90% dimethylsulphoxide. Ice-cold 4 N sodium hydroxide solution (~2.5 ml) was added until a pH of 9.5 was reached and approximately 20 ml of dimethylsulphoxide were added simultaneously, so that a dimethylsulphoxide concentration of ~90% was always maintained. After stirring for one hour at 4°, 30 mg of phenol were added to the reaction solution and, after a further 10 minutes, salts and the dimethylsulphoxide were removed by filtration through Sephadex G 10 using 0.1 M acetic acid as the eluting agent. 695 mg of an orange-coloured substance were obtained.

EXAMPLE 14

25 mg of 3,5-dichloroaniline (154 $\mu$ mols) were dissolved in 3 ml of 2 N hydrochloric acid and the diazonium salt thereof was prepared, as described in Example 2, with a solution of 12.5 mg of sodium nitrite (180 $\mu$ mols) in 50 $\mu$l of water. This diazonium salt solution was combined with a solution of 1 g of BPTI (154 $\mu$ mols) in 10 ml of water and the mixture was stirred, whilst cooling with ice, after adding 4 N sodium hydroxide solution until a pH value of 9.0 was reached. The pH of the reaction mixture was then adjusted to a value of 4.0 with acetic acid and the clear reaction solution was filtered through Sephadex G 10, using 0.1 M acetic acid as the eluting agent, in order to remove the salts. After the salt-free eluates containing protein had been freeze-dried, polymeric constituents—37 mg (4%)—were separated off by chromatography on Sephadex G 50 using 0.1 M acetic acid as the eluting agent. 850 mg (85%) of a yellow substance were obtained by freeze-drying the main fraction.

EXAMPLE 15

54 mg of p-amino cyclohexylbenzene (308 $\mu$ mols) were dissolved in 0.25 ml of glacial acid and were precipitated in a finely divided state by adding 5 ml of N hydrochloric acid, whilst stirring. 25 ml of sodium nitrite (362 $\mu$ mols) were added at 4° C. to the suspension, whilst stirring well, and 30 mg of amidosulphonic acid (309 $\mu$ mols) were added after 20 minutes and, after a further 5 minutes, the clear solution was combined with a solution of 1 g of BPTI in a 0.1 M borate buffer of pH 9.5. The pH of the solution was subsequently adjusted to a value of 9.5 with 4 N sodium hydroxide solution. A precipitate was immediately deposited from the red-coloured solution. After 15 minutes, a small quantity of phenol was introduced into the reaction mixture and glacial acetic acid was added to the latter until a pH value of 4.5 was reached. After removing undissolved matter by centrifuging—10 minutes, 3,000 g—the supernatant solution was freed from salts by filtration through Sephadex G 10 using 0.1 M acetic acid as the eluting agent. The higher-molecular constituents (55 mg, 6%), were separated off by chromatography of the salt-free lyophilisate on Sephadex G 50 (column: 2,5×100 cm), using 0.1 M acetic acid as the eluting agent. 825 mg (82%) of a yellow-orange coloured substance were obtained.

EXAMPLE 16

25 mg of sodium nitrite (360 $\mu$ mols) were added, as described in Example 1, to a solution of 42 mg of p-aminophenylacetamide (308 $\mu$ mols) in 5 ml of 2 N hydrochloric acid and the solution of the diazonium salt was combined, as described in Example 1, with a solution of 1 g of BPTI (154 $\mu$ mols) in 10 ml of water. The coupling reaction was carried out at pH 9.0, ad indicated in Example 1, and the dark reaction solution was freed from salts by filtration through Sephadex G 10. Higher-molecular constituents (52 mg, 5%) were separated off from the reaction mixture by chromatography on Sephadex G 50. 790 mg of an orange-coloured substance (79%) were produced on freeze-drying the main fraction.

EXAMPLE 17

A suspension of 60.5 mg of 2,4,5-trichloroaniline (308 $\mu$ mols) was obtained by precipitating the aniline derivative, dissolved in 0.5 ml of glacial acetic acid, by means of 5 ml of 2 N hydrochloric acid, and a solution of 25 mg of sodium nitrite (362 $\mu$ mols) in 0.1 ml of water was added at 4° C. whilst stirring well with a magnetic stirrer, whereupon a solution formed immediately. After 10 minutes, 20 mg of urea were added to the diazonium salt solution and the latter was combined, after a further 5 minutes, with a solution of 1 g of BPTI (154 $\mu$ mols) in 10 ml of water. The pH of the reaction mixture was adjusted to a value of 8.5 by adding 4 N sodium hydroxide solution. The solution immediately turned red and a precipitate formed. After stirring for 20 minutes in an ice bath, a small quantity of phenol was added to the reaction mixture and glacial acetic acid was added until a pH value of 4.5 was reached. The solution thus obtained was freed from salts by filtration through Sephadex G 10 using 0.1 M acetic acid as the eluting agent and the substance obtained after freeze-drying the eluates containing protein was chromatographed on Sephadex G 50, using 0.1 M acetic acid as the eluting agent, in order to separate off higher-molecular constituents (89 mg, 9%). 726 mg of an orange-coloured lyophilisate (73%) were finally obtained from the main fraction.

EXAMPLE 18

71 mg of 3,5-bis-trifluoromethyl-aniline (310 $\mu$ mols) were disslved in 250 $\mu$l of glacial acetic acid and were reprecipitated in a finely divided state by adding 5 ml of N hydrochloric acid, whilst stirring. A solution of 25 mg (362 $\mu$ mols) of sodium nitrite were added at 4° C. to the resulting suspension, whilst stirring well, and a clear diazonium salt solution was thus obtained. After stirring for 15 minutes whilst cooling with ice, a small quantity of amidosulphonic acid was added to the solution and it was combined, after a further 5 minutes, with a solution, pre-cooled to 4° C., of 1 g of BPTI (154 $\mu$ mols) in 10 ml of water. The pH of the solution was now adjusted to a value of 8.5 with ice-cold 4 N sodium hydroxide solution, a precipitate being formed immediately. After stirring for 15 minutes whilst cooling in ice, a small quantity of phenol was added to the reaction mixture and the pH of the latter was finally adjusted to a value of 5.0 with glacial acetic acid. The precipitate was removed by centrifugation and the supernatant solution was freed from salts by gel filtration through Sephadex G 10 using 0.1 M acetic acid as the eluting agent. After freeze-drying the eluates containing protein, 80 mg of polymers (8%) were separated off by chromatography on Sephadex G 50 and 780 mg of a yellow substance (78%) were obtained by freeze-drying the main fraction.

EXAMPLE 19

A solution of 25 mg of sodium nitrite (362 $\mu$ mols) in 0.1 ml of water was added at 4° C., whilst stirring well, to a suspension obtained by adding 5 ml of N hydrochloric acid to a solution of 44.5 mg of 3,4-dicyano-aniline (310 $\mu$ mols) in 0.25 ml of glacial acetic acid. After 15 minutes approximately 10 mg of solid amidosulphonic acid (103 $\mu$ mols) were added to the reaction solution and the latter was combined, after a further 5 minutes, with a solution, pre-cooled to 4° C., of 1 g of BPTI (154 $\mu$ mols) in 10 ml of water. 4 N Sodium hydroxide solution was added dropwise to the reaction solution until a pH of 8.8 was reached, whilst cooling and stirring well. An orange coloured precipitate soon formed. A small quantity of phenol was added to the reaction solution and glacial acetic acid was then added until a pH of 4.0 was reached. The undissolved material was removed by centrifuging (10 minutes/3,000 g) and the supernatant solution was freed from salts by filtration through Sepahdex G 10 using 0.1 M acetic acid as the solvent. 90 mg of higher-molecular constituents (9%) were separated off by chromatographing the lyophilisate on Sephadex G 50 using 0.2 M acetic acid as the eluting agent. 650 mg of an orange-coloured substance (65%) were obtained by freeze-drying the monomer fraction.

EXAMPLE 20

71 mg of p-amino-azobenzene (360 $\mu$ mols) were dissolved in 15 ml of a 1:2 mixture of propionic acid and acetic acid and, after cooling to $-10°$ C., 0.2 ml of concentrated sulphuric acid was added to the solution. 46 mg of nitrosylsulphuric acid (362 $\mu$ mols) were introduced at $-10°$ C. into the reaction mixture, whilst stirring, and 30 mg of urea (500 $\mu$ mols) were added after stirring for 30 minutes at $-10°$ C. After a further 30 minutes, the reaction mixture was combined with a solution of 1 g of BPTI (154 $\mu$ mols) in 10 ml of a 4 M urea solution and the pH value of the solution was adjusted to 8.8 with precooled 50% sodium hydroxide solution, whilst stirring and cooling. After 5 hours, glacial acetic acid was added to the mixture until a pH value of 4.0 was reached and the mixture was freed from salts by filtration through Sephadex G10, using 50% acetic acid. The polymeric constituents (78 mg, 8%) were separated off by chromatography on Sephadex G 50. 725 (72%) of a brown substance were obtained by freeze-drying the main fraction.

EXAMPLE 21

65 mg of 3-trifluoromethyl-4-fluoroaniline (360 $\mu$ mols) were dissolved in 5 ml of 2 N hydrochloric acid and diazotised at 4° C. by reaction with a solution of 27 mg of sodium nitrite (391 $\mu$ mols) in 0.25 ml of water. After 15 minutes the excess nitrite was destroyed by adding 10 mg of urea and the diazonium salt solution was combined, after 20 minutes, with a solution of 1 g of BPTI in 10 ml of water. The pH of the solution was adjusted to a value of 9.0 by adding ice-cold 4 N sodium hydroxide solution and it was left to stand for 20 minutes at 4° C. The pH of the reaction mixture was then adjusted to a value of 4 with acetic acid and the salts were removed by filtration through Sephadex G 10 using 0.1 M acetic acid as the eluting agent. After the fractions containing protein had been freeze-dried, polymeric constituents (56 mg, 6%) were removed by chromatography on Sephadex G 50. 802 mg (80%) of an orange-coloured substance were obtained by freeze-drying the main fraction.

EXAMPLE 22

78.0 mg of $\alpha$-aminopyrene (360 82 mols) were dissolved in a mixture of 1.5 ml of water and 100 $\mu$l of concentrated hydrochloric acid with heating. Whilst still hot, the solution was stirred into a mixture of 5 g of ice, 1 ml of water and 150 $\mu$l of concentrated hydrochloric acid, simultaneously with a solution of 25 mg of sodium nitrite (362 $\mu$ mols) in 150 ||l of water, in such a way that an excess of nitrite was avoided. After 30 minutes, the diazonium salt solution was combined with a solution of 1 g of BPTI (154 μ mols) in 5 ml of water and the pH of the solution was brought to a value of 8.5 by adding 4 N sodium hydroxide solution. The mixture was stirred for 1 hour at 4′ C. and was then diluted with 12 ml of glacial acetic acid and the reaction solution was filtered through Sephadex G 10 using 50% acetic acid as the eluant, in order to remove the salts and the low-molecular impurities. The dark fractions containing protein were freeze-dried. The polymeric constituents (18 mg, 2%) were separated therefrom by chromatograhy on Sephadex G 50 using 50% acetic acid as the eluting agent. 518 mg (52%) of an orange-red substance were obtained from the main fraction.

EXAMPLE 23

78 mg of aniline-3,5-disulphonic acid (310 μg) were dissolved in a mixture of 1 ml of glacial acetic acid and 1 ml of propionic acid by warming and, after cooling to −10° C., 0.2 ml of concentrated sulphuric acid was added. 51 mg of nitrosylsulphuric acid were then added, whilst stirring, to the suspension which had formed. After 15 minutes, 60 mg of urea were added to the mixture which was combined, after a further 15 minutes, with a solution of 1 g of BPTI (154 μ mols) in 10 ml of water. 4 N Sodium hydroxide solution was added to the reaction solution with cooling until a pH of 9.5 was reached, a precipitate being deposited. After 2 hours, glacial acetic acid was added to the reaction mixture until a clear solution was obtained—pH 3.5—. This solution was freed from salts via Sephadex G 10 using 0.1 M acetic acid as the eluting agent. The eluates containing protein were freeze-dried and polymeric constituents were separated off by chromatograhy on Sephadex G 50 using 50% acetic acid. 770 mg of an orange-coloured substance (77%) were isolated.

EXAMPLE 24

A solution of 25 ml of sodium nitrite (360 μ mols) in 150 μl of water was added dropwise at 4° C. and whilst stirring to asolution of 45 mg of 2,4-difluoroaniline (350 μ mols) in 5 ml of 2 N sulphuric acid. After 15 minutes, approximately 60 mg of urea were introduced into the reaction mixture. After a further 20 minutes, the solution of the diazonium salt was combined with a pre-cooled solution of 1 g of BPTI in 10 ml of 4 M urea solution and 4 N sodium hydroxide solution was then added until a pH of 9.0 was reached, an orange-coloured precipitate being deposited from the solution. After 10 hours, glacial acetic acid was added to the reaction mixture until a pH of 3.5 was reached and the solution, which was now clear, was freed from salts by filtration through Sephadex G 10 using 1 M acetic acid as the eluting agent. The fractions containing protein were chromatographed on Sephadex G 50 using 0.1 M acetic acid, in order to separate off polymeric by-products (85 mg, ∼8%). 780 mg of a yellow-red substance were obtained after lyophilisation of the main fraction.

EXAMPLE 25

44 mg of 3-chloroaniline (350 μ mols) were dissolved in 5 ml of 2 N sulphuric acid and converted at 4° C. into the diazonium salt, as described in Example 24, by adding a solution of 25 mg of sodium nitrite in 150 μl of water. After adding approximately 50 mg of urea, the reaction mixture was stirred for 20 minutes at 4° C. and the solution was finally combined with a solution of 1 g of BPTI in 10 ml of water. 4 N Sodium hydroxide solution was added to the reaction mixture until a pH value of 9.0 was reached and the suspension was kept at 4° C. for 10 hours. The pH of the mixture was then adjusted to a value of 3.5 with glacial acetic acid and the salts were removed by filtration through Sephadex G 10 using 1 M acetic acid as the eluting agent. After being concentrated by freeze-drying, the eluates containing protein were chromatographed on Sephadex G 50, using 1 M acetic acid as the eluting agent, in order to separate off polymeric constituents (33 mg∼3%), and 680 mg (68%) of an orange-coloured substance were isolated after freeze-drying the main fraction.

EXAMPLE 26

72 mg of 2,4-dinitroaniline (400 μ mols) were dissolved in 0.5 ml of glacial acetic acid by heating, the solution was poured onto 2 g of crushed ice and the precipitate was filtered off at once. The fine, yellow residue was added, whilst still moist, to a mixture of 0.6 ml of concentrated sulphuric acid and 0.15 ml of water. After cooling the reaction mixture to −5° C., a solution of 30 mg of sodium nitrite (435 μ mols) in 100 μl of water was added slowly from a micropipette under the surface, whilst stirring. After stirring for 5 hours at −3° C., 60 mg of urea were introduced into the solution and, after a further 20 minutes, the mixture was combined with a solution of 1 g of BPTI in 10 ml of water. Pre-cooled, 50% sodium hydroxide solution was now added to the reaction mixture until a pH of 8.5 was reached. In the course thereof, a yellow-orange coloured precipitate was deposited. After 5 hours, the reaction mixture was acidified with acetic acid to pH 3.5, a clear solution being obtained. The solution was filtered through Sephadex G 10, using 1 M acetic acid as the eluting agent, in order to remove salts, and the substance obtained on freeze-druying the eluates containing protein was chromatographed on Sephadex G 50, using 1 M acetic acid as the eluting agent, in order to separate off the polymeric constituents (91 ,h=9%). 782 mg (78%) of an orange-coloured substance were finally isolated.

EXAMPLE 27

50 mg of 3-nitroaniline (360 μ mols) were dissolved in 0.5 ml of glacial acetic acid and precipitated as the salt by stirring in 2 ml of water and 0.6 ml of concentrated sulphuric acid. After cooling the suspension to −2° C., the nitrite solution was stirred in under the surface as described in Example 26. After 2 hours, 50mg of urea were added to the clear solution and the mixture was combined, after a further 30 minutes, with a pre-cooled solution of 1 g of BPTI in 10 ml of water. 4 N Sodium hydroxide solution was now added to the reaction solution until its pH value had risen to 9.5. After 12 hours, glacial acetic acid was added to the suspension until a pH of 3.0 was reached. The practically clear solution was freed from salts by filtration through Sephadex G 10 using 0.1 M acetic acid as the eluting agent. After being concentrated by ultra-filtration through a Diaflow UM 2 membrane, the eluates containing protein were chromatographed on Sephadex G 50, using 50% acetic acid as the eluant, in order to separate off the polymeric constituents. 975 mg of an orange-coloured substance (79%) were obtained.

EXAMPLE 28

50 mg of 2-nitroaniline were diazotised analogously to Example 27 and the resulting diazonium salt solution was combined, at pH 9.5, with a solution of 1 g of BPTI in 10 ml of water, to effect coupling. After 48 hours, the reaction solution was freed from salts by filtration through Sephadex G 10. After being concentrated, the eluates containing protein were chromatographed on Sephadex G 50, using 0.1 M acetic acid as the eluting agent, and 758 mg of an orange-coloured substance (76%) were obtained.

EXAMPLE 29

A solution of 60 mg of 2,4-dicyano-3,5-dimethyl-1 aniline (350μ mols) in a mixture of 1 ml of glacial acetic acid and 1 ml of propionic acid was cooled to −5° C. and 0.2 ml of concentrated sulphuric acid was added. 51 mg of nitrosylsulphuric acid (401 μ mols) were added to the reaction mixture, whilst stirring, and the latter was stirred for 30 minutes at −5° to −10° C. 60 mg of urea were then introduced into the reaction solution and it was combined, after 20 minutes, with a solution of 1 g of BPTI (154 μ mols) in 10 ml of water. The pH of the coupling solution was adjusted to a value of 8.5 by adding pre-cooled 4 N sodium hydroxide solution, a precipitate being deposited immediately. After 6 hours, glacial acetic acid was added to the coupling mixture until a clear solution was obtained (pH 3.5); this clear solution was filtered through Sephadex G 10 in order to remove the salts. The polymeric constituents were separated off, as described in Example 1, by chromatography on Sephadex G 50, using acetic acid as the eluant (107 mg=11%). 765 mg of an orange-coloured substance (76%) were finally obtained.

EXAMPLE 30

A solution of 111 mg of 1-aminobenzene-4-(sulphonamidobenzene-4'-sulphonic acid) (350 μ mols) in a mixture of 1 ml of propionic acid and 1 ml of acetic acid was cooled and 0.2 ml of concentrated sulphuric acid was introduced, whilst stirring, followed by 63 mg of nitrosylsulphuric acid (496 μ mols), at −5° C. After 20 minutes, 60 mg of urea were added to the reaction solution and the latter was combined, after a further 20 minutes, with a solution of 1 g of BPTI (154 μ mols) in 10 ml of water. The pH of the coupling solution was adjusted to a value of 9.5 by adding pre-cooled 4 N sodium hydroxide solution and, after 5 hours stirring, glacial acetic acid was added at 4° C. to the mixture until a pH of 4.0 was reached. The reaction solution was then freed from salts by filtration through Sephadex G 10 using 1 M acetic acid as the eluting agent. Finally, after concentrating the eluates containing protein, the polymeric constituents were removed by chromatography on Sephadex G 50 using acetic acid as the eluting agent (72 mg; 7%). Finally, 858 mg (86%) of an orange-coloured substance were obtained from the main fraction.

EXAMPLE 31

60 mg of 2,4-dicyano-3,6-dimethyl-aniline (350 μ mols) were converted into the diazonium salt as described in Example 29. The solution of this diazonium salt was combined with a solution of 1 g of BPTI (154μ mols) in 10 ml of water and pre-cooled 4 M sodium hydroxide solution was added to the reaction solution until a pH of 8.5 was reached. After stirring for 20 hours at 4° C., the pH of the mixture was adjusted to a value of 4.0 with glacial acetic acid and the clear solution was freed from salts by filtration through Sephadex G 10 using 0.1 M acetic acid as the eluting agent. The freeze-dried eluates containing protein were chromatographed on Sephadex G 50 in order to separate off polymeric constituents. 753 mg (75%) of an orange-red substance were obtained as the main fraction.

EXAMPLE 32

65 mg of 2-trifluoromethyl-4-cyano-aniline (350 μ mols) were diazotised at −5° C. with nitrosylsulphuric acid, as described in Example 30. The diazonium salt solution was combined with a solution of 1 g of BPTI (154 μ mols) in 10 ml of water and the pH of the reaction mixture was adjusted to a value of 9.0 with 4 N sodium hydroxide solution. After 15 hours, glacial acetic acid was added to the reaction solution until it had an acidic reaction and the undissolved material was removed by centrifuging. The supernatant solution was concentrated to a small volume by ultra-filtration with the aid of a Diaflow UM 05 membrane and the retained fraction was combined with a solution, in 90% acetic acid of the residue from centrifuging. The acetic acid solution, which was approximately 50%, was freed from salts by filtration through Sephadex G 10 using 50% acetic acid as the eluting agent, and the eluates containing protein were chromatographed on Sephadex G 50, after concentration by freeze-drying, in order to separate off the polymeric constituents. 682 mg (68%) of an orange-coloured substance were obtained as the main fraction.

EXAMPLE 33

A diazonium compound was prepared, analogously to Example 30, by means of nitrosylsulphuric acid, from 81 mg of 5,6,7,8-tetrahydro-1-naphthylamine-4-sulphonic acid (360 μ mols). After destroying excess nitrosyl ions in the solution of the diazonium salt by adding urea, the solution was combined with a solution of 1 g of BPTI (154 μ mols) in 10 ml of 4 M urea solution and the coupling of the two components was carried out at pH 8.5. After 3.5 hours, glacial acetic acid was added to the reaction solution until a pH of 3.5 was reached and the solution was filtered through Sephadex G 10 in order to remove the salts. The eluates containing protein were lyophilised. The lyophilisate was dissolved in 10 ml of 50% acetic acid and was chromatographed on Sephadex G 50 using 1 M acetic acid as the eluting agent, in order to separate off the polymeric constituents. 755 mg of an orange-coloured substance (75%) were obtained as the main fraction, as well as 62 mg of polymeric constituents.

EXAMPLE 34

50 mg of 5-aminobenzimidazol-2-one (330 μ mols) were dissolved in 2 ml of 60% phosphoric acid by warming; a solution of 25 mg of sodium nitrite (362 μ mols) in 100 μl of water was added to the solution at 4° C., whilst stirring well and the mixture was stirred for 15 minutes at 4° C. 30 mg of urea (500 μ mols) were then added to the reaction solution and it was combined, after a further 15 minutes, with a pre-cooled solution of 1 g of BPTI in 10 ml of 5 M urea solution. The pH of the reaction solution was adjusted to a value of 9.5 by adding 50% sodium hydroxide solution and it was stirred for 5 hours at 4° C. Glacial acetic acid was then added to the mixture until the pH was 4.5 and the mixture was filtered through Sephadex G 10 in order to remove the urea and the salts. Residual salts were finally removed, after lyophilising, by dialysis in an acetylated Visking tubing. The retained fraction was chromatographed on Sephadex G 50 using 50% acetic acid as the eluting agent. 695 mg (69% of an orange-brown substance were obtained as the main fraction.

EXAMPLE 35

61 mg of 6-amino-2,3-dihydro-1,2-benzisosulphonazol-3-one=6-aminosaccharin (310 $\mu$ mols) were suspended in a mixture of 1 ml of glacial acetic acid, 1 ml of propionic acid and 0.2 ml of concentrated sulphuric acid and the mixture was stirred for 30 minutes at $-10°$ C. with 50.8 mg of nitrosylsulphuric acid (400 $\mu$ mols). Approximately 60 mg of urea were then added to the reaction mixture, followed, after a further 15 minutes, by a solution of 1 g of BPTI (154 $\mu$ mols) in 10 ml of 4 M urea solution. 4 N Sodium hydroxide solution was added until a pH of 9.0 was reached and the coupling mixture was kept for 1 hour at 4° C., whilst stirring. The reaction solution was then filtered through Sephadex G 10 and dialysed in an acetylated Visking dialysing tubing in order to remove the residual salts, and the retained fraction was concentrated to a small volume by ultra-filtration through a UM-2 filter. An equal volume of glacial acetic acid was added to the retained fraction, which was partially undissolved, and the solution was chromatographed on Sephadex G 50, using 50 percent acetic acid as the eluting agent, in order to separate off the polymeric constituents (41 mg=4%) and 830 mg (83%) of an orange-coloured substance were isolated as the main fraction.

EXAMPLE 36

A solution of 250 mg of sodium nitrite (3.6 mmols) in 0.5 ml of water was added dropwise at 4° C., whilst stirring well, to a solution of 270 mg of 5-amino-1,H-tetrazole (3.2 mmols) in 4.5 ml of N hydrochloric acid. After 15 minutes, 120 mg of urea (2 mmols) were added to the reaction mixture and it was combined, after a further 10 minutes, with a solution of 1 g of BPTI (154 $\mu$ mols) in 10 ml of a 6 M urea solution. Ice-cold, 50% sodium hydroxide solution was now added to the solution until a pH of 4.5–5.0 was reached and the solution was stirred for 5 hours at 4° C. 120 mg of phenol (2 mmols) were then added to the reaction solution and, after a further 15 minutes, it was freed from salts by filtration through Sephadex G 10 using 50% acetic acid as the eluting agent. After concentrating the salt-free filtrate by freeze-drying, polymeric constituents (120 mg=12%) were separated off by chromatography on Sephadex G 50 using 50% acetic acid as the eluting agent. After freeze-drying the main fraction, 682 mg (62%) of a violet substance were obtained.

EXAMPLE 37

50 mg of 3,5-dichloroaniline were converted, as described in Example 10, into the diazonium compound and the resulting solution was combined at 4° C. with a solution of 1 g of desamido-BPTI-obtained by allowing BPTI to stand for 20 days in 1 N hydrochloric acid at 4° C. -in 15 ml of a borate buffer of pH 9.5. After 1 hour, a small quantity of phenol was added to the reaction solution and, after a further 5 minutes, acetic acid was added until the pH reached a value of 3.5. The solution was filtered through Sephadex G 10, using 0.1 M acetic acid as the eluting agent, in order to free it from salts and polymeric constituents were separated off from the concentrated eluates containing protein by chromatography on Sephadex G 50 using 0.1 M acetic acid as the eluting agent. 752 mg of an orange-coloured substance (75%) were obtained by freeze-drying the eluates containing the monomers.

EXAMPLE 38

A solution of 52 mg of sodium nitrite (752 $\mu$ mols) in 0.2 ml of water was added at 4° C., whilst stirring well, to a solution of 58 mg of 5-amino-1,H-tetrazole (675 $\mu$ mols) in 10 ml of N hydrochloric acid, and the mixture was kept under ice-cooling for 15 minutes. 20 mg of urea ($\sim$200 $\mu$ mols) were then added and the solution was combined with a solution, precooled to 4° C., of 2 g of BPTI (308 $\mu$ mols) in 15 ml of water. The pH of the mixture was adjusted to a value of 8.6 with 4 N sodium hydroxide solution and the intensely yellow solution was stirred for 15 minutes whilst cooling with ice. After adding a small quantity of phenol, the reaction solution was chromatographed on Sephadex G 10, using 0.1 M acetic acid as the eluting agent, in order to separate off the salts. 1.85 g of a colourless substance were isolated by freeze-drying the eluates containing protein. This substance was dissolved in 20 ml of 0.1 N NaOH and the solution was cooled to 4° C. and combined with a diazonium salt solution prepared, in accordance with Example 10, from 100 mg of 3,5-dichloroaniline. Concentrated sodium hydroxide solution was added to the reaction mixture until a pH value of 9.2 was reached, whereupon a precipitate was deposited immediately with the production of a red colour. After 15 minutes, a small quantity of phenol was added to the solution and it was freed from the salts by filtration through Sephadex G 10 using 1 M acetic acid as the eluting agent. The lyophilisate was then chromatographed on Sephadex G 50, using 0.1 M acetic acid as the eluting agent, in order to separate off the higher-molecular constituents. In addition to 128 mg of polymeric constituents (6%), 1560 mg of the orange-red monomers (78%) were obtained.

EXAMPLE 39

200 ml of a 2 M sodium nitrite solution were added dropwise in the course of 30 minutes, at 0°–4° C., whilst stirring well and maintaining an atmosphere of nitrogen, to a solution of 2 g of BPTI (307$\mu$ mols) in 800 ml of oxygen-free, 0.25 M acetic acid. In the course thereof, the pH value of the solution rose from 3.7 to 4.1. After 24 hours, the volume of the reaction solution was reduced to 500 ml by ultrafiltration in an Amicon ultra-filtration cell with the aid of a Diaflow UM-05 membrane, and the retained fraction was freed from salts by filtration through Sephadex G 10. (Column: 2.5$\times$150 cm.)

The salt-free lyophilisate was dissolved in 15 ml of water and the solution was cooled to 4° C. and then combined with a diazonium salt solution obtained, in accordance withh Example 10, from 100 mg of 3,5-dichloroaniline. After a coupling reaction carrid out as in Example 10, the reaction solution was freed from salts by a Sephadex G 10 filtration, using 50% acetic acid as the eluting agent. Higher molecular constituents were separated off by chromatography on Sephadex G 50 using 50% acetic acid. (120 mg, $\sim$6%). 1230 mg (61%) of an orange-coloured substance where obtained after freeze-drying the main faction.

EXAMPLE 40

1 g of BPTI (154 $\mu$ mols) was dissolved in 400 ml of ice-cold, oxygen-free, C., 0.25$^m$ acetic acid. 100 ml of 2 N sodium nitrite solution were added dropwise at 4° C., in the course of 30 minutes, whilst passing nitrogen through and stirring well, and the reaction mixture was then kept at 4° C. for 24 hours; in the course thereof the pH value of the solution rose from 3.7 to 4.1. The pH of the solution was adjusted to 9.0 with concentated ammonia solution and was then concentrated in an Amicon ultra-filtration cell by means of a Diaflow UM 05 membrane and was freed from salts. Higher-molecular constituents were removed by chromatography on Sephadex G 50; the main fraction was lyophilised. 500 mg of this lyophilisate, which contains desamino derivatives of BPTI, were dissolved in 10 ml of water and combined with a solution of 25 mg of 3,5-dichloroaniline, diazotised in accordance with Example 10. The pH was adjusted to a value of 9.0, the mixture was stirred for 5 hours at 4° C., a small quantity of phenol was added and the pH was again adjusted to a value of 3.5 with glacial acetic acid. The solution was gel filtered through Sephadex G 10, using 0.1 M acetic acid as the eluting agent, in order to remove the salts and low-molecular by-products. The protein-containing fractions were concentrated to a small volume by ultra-filtration and chromatographed on Sephadex G 50, using 50% acetic acid as the eluting agent in order to separate off polymeric constituents (26 mg, 5%). 318 mg (63%) of an orange-coloured substance were obtained after freeze-drying the main fraction.

EXAMPLE 41

1 g of BPTI was reacted as in Example 40 with $NaNO_2$ in an acid medium. After 24 hours, the reaction mixture was worked up as in Example 40—without correcting the pH value—by ultra-filtration, gel filtration through Sephadex G 50 and freeze-drying. 380 mg of the main fraction, which contained mononitro-desamine-BPTI derivatives, were dissolved in 10 ml of 4 M urea solution and combined with a solution of 24 mg of 3,5-dichloroaniline, diazotised in accordance with Example 10. The pH of the mixture was adjusted to of 9.5, stirred at 4° C. for 10 hours and then gel filtered through Sephadex G 10 using 50% acetic acid as the eluant. The lyophilisate of the protein-containing fractions was completely freed from salts by dialysis in acethylated Visking tubing. The retained fraction, which contained undissolved constituents, was then diluted with an equal volume of glacial acetic acid and chromatographed on Sephadex G 50 in order to separate off polymeric constituents (25 mg, 7%). 280 mg of an orange-coloured product (74%) were obtained as the main fraction.

EXAMPLE 42

750 mg of azo-BPTI derivative (115 $\mu$ mols), obtained in accordance with Example 11, were dissolved in 150 ml of 0.1 M trishydroxymethylaminomethane/-hydrochloric acid buffer of pH 8.0, and a mixture of 10 g of tetranitromethane and 12 ml of ethanol was added whilst stirring. The reaction solution was stirred for 3 hours at pH 8.0 concentrated hydrochloric acid was then added until a pH of 4.8 was reached. The volume of the solution was then reduced to 10 ml by ultra-filtraton through a UM 2 membrane and the solution was freed from salts by filtration through Sephadex G 10 using 50% acetic acid as the solvent. After freeze-drying the eluates containing protein, the polymeric constituents (131 mg, ~17%) were separated off by chromatography on Sephadex G 50 using 50% acetic acid and 555 mg (74%) of an orange-red substance were obtained by freeze-drying the main fraction.

EXAMPLE 43

(a) Nitration of BPTI with nitric acid to give mononitro-BPTI:

10 ml of concentrated nitric acid were added to a solution of 2.5 g of BPTI (385 $\mu$ mols) in 100 ml of 1 M acetic acid and the mixture was kept at 20° C. for 24 hours and at 4° C. for a further 24 hours. 25 ml of concentrated aqueous ammonia solution were than added to the reaction mixture and the volume of the latter was concentrated to approximately 25 ml by ultra-filtration through an Amicon UM 05 membrane. The concentrate was now freed from salts by filtration through Sephadex G 10 using 0.1 M acetic acid and the eluates containing protein were buffed against 0.1 M sodium chloride/0.1 M trishydroxy-methyl-aminomethane hydrochloride buffer of pH 7.2. 1.2 g of mononitro-BPTI, as well as a smaller quantity of a dinitro-BPTI derivative (0.62 g) were obtained by chromatography on CM-Sephadex by the method of B. Meloun, I. Fric and F. Sorm [Europ, J. Biochem. 4, 112 (1968)].

(b) Coupling with diazotised 3,5-dichloroaniline:

The diazonium salt was prepared, as described in Example 10, from 58 mg of 3,5-dichloroaniline (360 $\mu$ mols) and was reacted for 3 hours at pH 9.5 with 1 g (154 $\mu$ mols) of the above mononitro-BPTI. After the reaction solution had been freed from salts by filtration through Sephadex G 10 using 0.1 M acetic acid as the eluting agent, the polymeric constituents (68 mg, ~7%) were separated off by chromatography on Sephadex G 50 using 0.1 M acetic acid as the eluting agent. 825 mg (82%) of an orange-coloured substance were isolated as the main fraction by freeze-drying.

EXAMPLE 44

Citraconylation:

A solution of 1.3 g (0.2 mmol) of BPTI in 25 ml of 0.1 M borax solution was cooled to 4° C. and a total of 0.52 ml of citraconic anhydride was added dropwise, the pH value of the reaction mixture being kept constant at 8.0, which, if necessary, was achieved by adding 30% NaOh, Diazotisation:

0.6 mmol of 3-amino-1-H-1,2,4-triazole were dissolved in 0.6 ml of glacial acetic acid and a mixture of 1.3 ml of phosphoric acid (approximately 80%d=1.171) and 5 ml of ice/water was added. 50 mg of $NaNO_2$, dissolved in 1 ml of water, were added to this solution whilst stirring. The reaction mixture was stirred for 10 minutes, 20 mg of amidosulphonic acid were then added and stirring was then continued for a further 5 minutes.

Coupling:

This diazotisation mixture was added to the solution of the citracnylated BPTI, which was still cooled, the pH was adjusted to a value of 7.5 with 30% NaOH, the reaction mixture was stirred at 4° C. for 60 minutes, 250 mg of mono-N-butyryltyrosine, DCHA salt was then introduced and stirring was continued for a further 30 minutes. Splitting off the citraconyl groups: Solid citric acid was added until the pH value of the reaction mixture reached approximately 4 and this value was then adjusted to precisely 3.5 with concentrated HCl. The mixture was then allowed to stand at room temperature for 20 hours.

Working up:

Sufficient glacial acetic acid was added to the mixture to re-dissolve a precipitate which had meanwhile been deposited. The mixture was then gel filtered, using 5% acetic acid as the eluting agent, through a gel bed of 400 ml of Sephadex G 15 which has been buffered with 5% acetic acid. The protein-containing fractions were lyophilised. The lyophilisate was one more dissolved in 5% acetic acid and was again gel filtered under the conditions just described. After the protein-containing fractions had been lyophilised again, 960 mg of a solid substance having a protein content of 87% were obtained.

EXAMPLE 45

1.3 g of BPTI were citraconylated as in Example 44. 0.6 mmol of aminotetrazole, instead of aminotriazole, was diazotised as in Example 44.

This diazotisation mixture was reacted as in Example 44 with the citraconylated BPTI in a coupling reaction. The citraconyl groups were split off and the mixture was worked up as described in Example 44. 820 mg of a lyophilisate having a protein content of 89% were obtained as the end product.

EXAMPLE 46

1300 mg of BPTI were citraconylated as in Example 44. 0.6 mmol of sulphanilic acid sulphanilide was diazotised by dissolving it in 1.1 ml of 0.6 M NaOH, adding 50 mg of $NaNO_2$, dissolved in 1 ml of water, and adding the mixture, whilst shaking, to a mixture of 1.3 ml of concentrated phosphoric acid (d=1.71) and 5 ml of ice/water. The mixture was shaken for 10 minutes, 20 mg of amidosulphonic acid were added and shaking was continued for a further 5 minutes.

The coupling with the citraconylated BPTI, the splitting off of the citraconyl groups and the working up of the mixture were carried out as described in -dichloroaniline 44. 920 mg of a lyophilisate having a protein content of 89% were obtained as the end product.

EXAMPLE 47

1.3 g of BPTI were citraconylated as in Example 44. 0.6 mmol of 3,5-dichloraniline was diazotised analogously to Example 47.

The diazotisation mixture was reacted, as in Example 44, with the citraconylated BPTI in a coupling reaction. The citraconyl groups were than split off as in Example 44.

The mixture was then acidified with acetic acid as in Example 44. In spite of this, considerable quantities remained undissolved and were then filtered off and discarded. The filtrate was purified, as in Example 44, by two gel filtrations on Sephadex G 15. 250 mg of a lyophilisate having a protein content of 89% were finally obtained.

EXAMPLE 48

1.3 g of BPTI were citraconylated as in Example 44. 0.6 mmol of aminobenzene-3,5-disulphonic aicd was dissolved in 1.5 ml of 1 M NaOH; 50 mg of $NaNO_2$ were added to the solution and were also dissolved. The diazotisation was carried out, as in Example 46, by adding phsophoric acid.

The coupling reaction with the citraconylated BPTI, the splitting off of the citraconyl groups and the working up were carried out as described in Example 44. 1100 mg of a lyophilisate having a protein content of 95% were obtained as the end product.

EXAMPLE 49

1.3 g of BPTI were citraconylated as in Example 44. 0.6 mmol of 1-(p-aminophenyl)-3,5-dichloro-1,2,4-triazole was diazotised analogously to Example 44.

The diazotisation mixture was reacted, as in Example 44, with the citraconylated BPTI in a coupling reaction. After splitting off the citraconyl groups as in Example 44, the whole mixture was worked up by two gel filtrations on Sephadex G 15, as described under 44. A lyophilisate of 1170 mg, containing 74% of protein, was finally obtained.

EXAMPLE 50

The procedure followed was as in Example 49, with the sole difference that 15 g of solid urea were added to the solution of the citraconlylated BPTI before the coupling reaction.

1030 mg of a lyophilisate having a protein content of 100% were produced as the end product.

EXAMPLE 51

1.3 g of BPTI were citraconylated as in Example 44. 0.6 mmol of sulphanilic acid was diazotised analogously to Example 46.

The coupling reaction, the splitting off of the citraconyl groups and the working up of the reaction mixture were carried out as in Example 44. 1130 mg of a lyophilisate having a protein content of 100% were finally obtained.

Example 52

1.3 g of BPTI were citraconylated as described in Example 44. 15 g of urea were added to this mixture. 0.6 mmol of p-aminobenzoic acid was diazotised analogously to Example 46.

The coupling reaction, the splitting off of the citraconyl groups and the working up of the reaction mixture are carreid out as in Example 44. 700 mg of a lyophilisate having a protein content of 88% were finally obtained.

EXAMPLE 53

650 mg (100 μ mols) of a mixture of nitrated BPTI [B. Meloun, I. Frič and F. Sorm, Europ. J. Biochem. 4, 112 (1968)] were dissolved in 25 ml of M tris-(hydroxymethyl)-aminomethane buffer of pH 7.5. Two portions of 300 mg each of sodium dithionite were added to the solution with an interval of 10 minutes, whilst stirring well and acetic acid was added to the mixture 10 minutes after the last addition until a pH value of 5.0 was reached. The reaction mixture was freed from salts by filtering through Sephadex G 10 using 0.1 M acetic acid as the elutting agent. The eluates containing protein were freeze-dried. The lyophilisate was dissolved in 5 ml of N hydrochloric acid and a solution of 14 mg of sodium nitrite (203 μ mols) in 100 μof water was added to the solution, after cooling to 4° C., whilst stirring well. After 10 minutes, 10 mg of solid amidosulphonic acid were added to the solution followed, after a further 5 minutes, by a pre-cooled solution of 94 mg (1 mmol) of phenol in 5 ml of N sodium hydroxide solution (pH 8.2). The yellow suspension was stirred whilst sodium hydroxide solution until a pH value of 9.0 was reached. A red solution was obtained in the course of 30 minutes. After adding acetic acid until the pH was 4.0, the reaction solution was freed from salts by chromatography on Sephadex G 10. The higher-molecular constituents were then separated off by chromatographing the eluates containing protein on Sephadex G 50 using 0.1 M acetic acid as the eluting agent. 425 mg of a yellow-orange substance were finally obtained.

EXAMPLE 54

750 mg of a mixture of mononitro-BPTI and dinitro-BPTI were treated with dithionite as described in Example 53. The reaction solution was concentrated by ultra-filtration through a Diaflow UM 05 membrane and was freed from salts and was finally filtered through Sephadex G 10. On lyophilising the eluates containing protein, 630 mg of a colourless substance were obtained, which were dissolved in 10 ml of 6 M urea solution.

The ice-cold solution of the mixture of mono- and di-3-amino-tyrosyl-BPTI thus obtained was combined with a diazonium salt solution prepared, in accordance with Example 12, from 50 mg of 3,5-dichloroaniline and the pH of the reaction mixture was adjusted, by adding 8 M sodium hydroxide solution, first to a value of 4.0 and, after 15 minutes, to a value of 5.0. After 60 minutes, the brown solution was freed from salts by filtration through Sephadex G 10 using 50 percent strength acetic acid. The polymeric constituents were then separated off by chromatographing the eluates containing protein on Sephadex G 50, using 50% acetic acid as the eluting agent (60 mg, 9%). 480 mg of an orange-coloured substance (76%) were obtained by lyophilising the main fraction.

EXAMPLE 55

51 mg of 5-aminobenztriazole (380 $\mu$mols) were dissolved in 2.5 ml of 60% phosphoric acid by warming. A solution of 29 mg of sodium nitrite (410 $\mu$ mols) in 250 $\mu$l of water was added to this solution at 4° C., whilst stirring. After 10 minutes, 60 mg of urea (1 mmol) were added to the solution of the diazonium salt and it was combined, after a further 15 minutes, with a pre-cooled solution of 1 g of BPTI (154 $\mu$ mols) in 10 ml of water. The pH of the coupling solution was adjusted to a value of 9.0 with ice-cold 8 N sodium hydroxide solution and the reaction mixture was stirred at 4° C. for 3 hours. Glacial acetic acid was then added until a pH value of 4.0 was reached and undissolved constituents were removed by centrifuging—10 minutes, 2000 mg.—The supernatant solution was freed from salts by filtration through Sephadex G 10, using 1 M acetic acid. 93 mg (9%) of higher-molecular constituents were separated off by chromatographing the eluates containing protein on Sephadex G 50. 723 mg (72%) of an orange-coloured substance were obtained.

EXAMPLE 56

1 g of NaNO$_2$ was dissolved in 14 ml of boiled water. After cooling this solution to 4° C., 0.5 g of azo-BPTI derivative, obtained in accordance with Examples 48, was introduced little by little. After it had dissolved, sufficient citric acid was additionally dissolved to give a pH value of 5.0. The pH was then adjusted to a value of 4.0 with approximately 10% hydrochloric acid. The reaction vessel was evacuated and allowed to stand at 4° C. for 24 hours.

The mixture was then diluted with 10 ml of H$_2$O, the pH was adjusted to a value of 8.5 with 10% imidazole solution, small quantities of insoluble constituents were filtered off and the filtrate was gel filtered through a Sephadex G 15 column (25 ml gel bed, buffered with 0.1 M NH$_4$HCO$_3$ solution), using 0.1 M NH$_4$HCO$_3$ solution as the eluting agent. The protein-containing fractions were lyophilised. 400 mg of a lyophilisate having a protein content of 78% were obtained.

EXAMPLE 57

70 mg of 3,6-dimethoxyaniline (460 $\mu$ mols) were dissolved in 2.5 ml of 2 N sulphuric acid. A solution of 35 mg of sodium nitrite in 100 $\mu$l of water was added at 2° C. to this solution, whilst stirring. The reaction mixture was stirred for 20 minutes at 0–4° C., 60 mg of urea were then added and the mixture was combined with a solution, pre-cooled to 4° C, of 1 g of BPTI in 10 ml of a 6 M urea solution. 8 N NaOH was then added to the solution until a pH of 8.5 was reached and the suspension was stirred for 3 hours at 4° C. 10 ml of glacial acetic acid were then added to the mixture and the solution was freed from salts by filtration through Sephadex G 10 using 50% acetic acid as the eluting solvent. After freeze-drying, the protein-containing eluates were chromatogaphed on Sephadex G 50, using 50% acetic acid as the eluting agent, in order to separate off higher-molecular constituents (80 mg). 783 mg (78%) of a red-brown substance were obtained as the main fraction.

EXAMPLE 58

100 mg of 2,3-dimethylaniline (800 $\mu$ mols) were dissolved in 1 ml of 80% phosphoric acid. A solution of 63 mg of sodium nitrite in 200 $\mu$l of water was added dropwise, whilst stirring, to the solution, which had been cooled to 2° C., and 20 mg of amidosulphonic acid were added to the mixture after 10 minutes. After stirring for a further 10 minutes, the mixture was combined with a solution of 1.3 g of BPTI (200 $\mu$ mols) in 10 ml of 0.1 M borate buffer of pH 9.0. The pH of the mixture was adjusted to a value of 8.5 by adding 8 N NAOH and 10 Ml of glacial acetic acid were added to the orange-coloured suspension after 1 hour. The solution was freed from salts by filtration through Sephadex G 10 using 50 acetic acid. 930 mg of an orange coloured substance (72%) were obtained.

EXAMPLE 59

123 mg of 2,4-dimethoxyaniline (800 $\mu$ mols) were diazotised, analogously to Example 58, under a N$_2$ atmosphere. After destroying the excess nitrous acid with 50 mg of urea, the solution of the diazonium salt was added to a solution of 1.3 g of BPTI in 10 ml of 0.1 M borate buffer of pH 9.0, and the pH of the mixture was adjusted to a value of 8.5 with 8 M NaOH. In the course thereof the mixture turned dark brown. After 1 hour, 20 mg of phenol were added and, finally, after a further 10 minutes, 10 ml of glacial acetic acid were added and the coupling solution was freed from salts by filtration through Sephadex G 10 using 50% acetic acid as the solvent. 950 mg of a brown-orange substance (73%) were obtained.

EXAMPLE 60

Methylation: By analogy with the method of G. E. Means and R. E. Feeney [Biochemistry 7, 2192 (1968)], 1 g of BPTI (154 $\mu$ mols) were dissolved in 100 ml of 0.05 M borate buffer of pH 9.0. 50 mg of sodium borohydride and 50 $\mu$l of 35% formaldehyde solution were added at 0° C., whilst stirring well, to the reaction mixture followed by a further three portions of 50 $\mu$l each of formaldehyde solution at intervals of 5 minutes. After 30 minutes and also after a further 15 minutes, 50 mg of sodium borohydride and 50 μl of formaldehyde solution were again added, each time. Acetic acid was then added to the reaction solution until a pH of 6.0 was reached and the volume of the solution was reduced to 10 ml by ultra-filtration through an UM 05 filter. After being freed from salts on Sephadex G 10 using 0.1 M acetic acid, the protein-containing fractions were freeze-dried. 705 mg (70%) of a colourless substance were obtained; according to the process of A.F.S.A. Habeeb. Analytical Biochem. 14,328 (1966), the content of end groups, as determined by 2,4,6-trinitrobenzene-sulphonic acid, was 20% of the initial value.

Coupling with diazotised 3,5-dichloroaniline: 500 mg of the above methylated BPTI derivative were dissolved in 5 ml of water and this solution was combined with a solution of the diazonium compound which had been prepared from 50 mg of 3,5-dichloroaniline by diazotisation in accordance with Example 11. The pH of the mixture was adjusted to a value of 8.5 with 8 N NaOH. In the course thereof an intensely brown-red suspension was formed. After 30 minutes, 20 mg of phenol were added and, finally, 10 ml of glacial acetic acid were added. The clear solution was filtered through Sephadex G 10 using 50% acetic acid in order to remove the salts and low-molecular impurities. 375 mg of an orange-red substance (75%) were obtained after separating off polymeric constituents by chromatography on Sephadex G 50 using 50% acetic acid.

EXAMPLE 61

500 mg of guanidated BPTI (B. Kassell and R. B. Chow, Biochemistry 5, 3449–3453 [1960]; J. Chauvet and R Acher, Biochem. Biophys. Res. Comm. 27, 230–235 [1967]) were dissolved in 7.5 ml of 0.1 M borate buffer of pH 9.5 which was 6M in respect to urea. This solution was combined at 0° C. with the solution of the diazonium salt which had been prepared, in accordance with Example 11, from 50 mg of 3,5-dichloroaniline, and 8 N NaOH was added to the mixture until a pH value of 8.5 was reached. After stirring for 30 minutes with ice-cooling, 50 mg of phenol were added to the mixture, followed by 10 ml of glacial acetic acid. The mixture was freed from salts by chromatographing on Sephadex G 10 using 50% acetic acid as the solvent. 416 mg (83%) of a red-orange substance were obtained after lyophilising the main fraction.

EXAMPLE 62

800 mg of BPTI which had been only partially guanidated were dissolved in 20 ml of 0.1 M borate buffer of pH 9.0. 500 mg of succinic anhydride were introduced in 5 equal portions into this solution of 4° C. and whilst stirring well, the pH value of the mixture being kept at pH 8.5–9.0 by adding 8 N NaOH. The diazonium salt solution which had been prepared, analogously to Example 11, by diazotising 100 mg of 3,5-dichloroaniline were added 1 hour after the last addition of the succinic anhydride. During the coupling a pH value of ~8.0 was maintained by adding 8 N NaOH. 50 mg of phenol were added to the brown suspension after 1 hour. The suspension were rendered weakly acid with glacial acetic acid and the precipitate was removed by centrifuging—2000 g/10 minutes—. The supernatant solution was concentrated to 5 ml by ultra-filtration and the retained fraction was dissolved, together with the sediment from the centrifuging, by adding glacial acetic acid. The solution was freed from salts by filtration through Sephadex G 10 using 50% acetic acid as the solvent and 700 mg (88%) of a brown-red substance were obtained by freeze-drying.

EXAMPLE 63

1.3 g of the azo derivative of BPTI (200 μ mols), which has been obtained in accordance with Example 36 and had at the same time been partially deaminated, were suspended in 20 ml of 0.1 M borate buffer of pH 9.0, and 500 mg of succinic anhydride were introduced into the mixture in 10 portions, in the course of 1 hour, at 4° C. and whilst stirring well. A clear, olive-green solution was formed immediately. During the reaction the pH of the reaction solution was kept at a value of 9.0 by adding 8 N NaOH. After a reaction lasting altogether 2 hours, the mixture was filtered through Sephadex g 10 using 0.1 M ammonium hydroxide solution as the eluting agent and 1.10 g (85%) of a dark brown substance were obtained after freeze-drying the first coloured eluates.

What is claimed is:

1. A derivative of kallikrein-trypsin inhibitor (BPTI) in which the 10—and/or 21—trypsin residue is linked, in the ortho-position relative to the phenolic hydroxyl group, to a mononuclear or polynuclear aromatic carbocyclic or heterocyclic radical, which in turn can be unsubstituted or substituted by alkyl, alkoxy, sulfonic acid, sulfonyl, carboxyl, nitro, cyano, trifluoromethyl, chloro groups or atoms via an azo group.

2. A derivative of kallikrein-trypsin inhibitor (BPTI) in which one of the 10—or 21—tyrosin residues is linked, in the o-position relative to the phenolic hydroxyl group, to a mononuclear carbocyclic aromatic or heterocyclic radical which can be unsubstituted or substituted by alkyl, alkoxy, sulfonic acid, sulfonyl, carboxyl, nitro, cyano, trifluormethyl, chloro groups or atoms via an azo group and the other of the said tyrosine residues carries a nitro group in the o-position relative to the phenolic hydroxyl group.

3. A derivative according to claim 1 which is partially or completely deaminated.

4. A derivative according to claim 1 which is partially or completely deamidized.

5. A derivative according to claim 1 in which the aliphatic amino groups are additional partially or completely guanidated, amidated, carbamylated, acylated or alkylated.

6. A derivative according to claim 1 in which some of the free amino groups are additionally deaminated and at the same time, other amino groups are guanidated, amidated, carbamylated, acylated or alylated.

7. A derivative according to claim 1 which is partially or completely deaminated and in addition is also partially or completely deamidized.

8. A derivative according to claim 1 containing aliphatic amino groups which is partially or completely substituted and which at the same time, is partially or completely deamidized.

9. A derivative according to claim 1 wherein some of the free amino groups are additionally deaminated and other amino grups are substituted, the derivative at the same time being partially or completely deamidized.

10. A pharmaceutical composition containing, as an active ingredient, an effective amount of a derivative according to claim 1 in admixture with a solid or liquefied gaseous diluent or in admixture with a liquid diluent.

11. A pharmaceutical composition containing, as an active ingredient, an effective amount of a derivative according to claim 1 in the form of a sterile or isotonic aqeuous solution.

12. A composition according to claim 10 containing from 0.5 to 95% by weight of the said active ingredient.

13. A composition according to claim 11 containing from 0.5 to 95% by weight of the said active ingredient.

14. A medicament, in unit dosage form, comprising an effective amount of a derivative according to claim 1 and an inert pharmaceutical carrier.

15. A medicament of claim 14 in the form of tablets, pills, dragees, capsules, ampoules, or suppositories.

16. A method of combating diseases caused by overproduction of proteases or by a deficiency of indigenous protease inhibitors in warm-blooded animals which comprises administering to the animals a derivative in an amount of from about 0.1 to 40 mg. per kg body weight per day according to claim 1 either alone or in admixture with a diluent or in the form of a medicament.

17. A derivative of kallikrein-trypsin inhibitor (BPTI) bearing an amino group in the ortho-position relative to the phenolic hydroxyl group on the 10—and/or 21—tyrosine residues and an optionally substituted aromatic or heterocyclic residue which is linked via an azo group in the meta position relative to the phenolic hydroxyl group on the 10—and/or 21—residues.

* * * * *

UNITED STATES PATENT AND TRADEMARK OFFICE
CERTIFICATE OF CORRECTION

PATENT NO. : 4,153,687

DATED : May 8, 1979

INVENTOR(S) : Eugen Schnabel, et al.

It is certified that error appears in the above-identified patent and that said Letters Patent are hereby corrected as shown below:

```
Title Page, "Tscheschl" should be --Tschesche--.
Column 2, line 20, "and" should be --or--.
Column 5, line 19, "Jager" should be --Jäger--.
Column 5, line 46, "Wunsch" should be --Wünsch--.
Column 5, line 49, "Muller" should be --Müller--.
Column 6, line 28, "Azo" should be --azo--.
Column 7, line 40, "Putter" should be --Pütter--.
Column 7, line 43, "Muller" should be --Müller--.
Column 9, line 37, "Table I" should be --Table 2--.
Column 9, line 39, insert "mols" in title of column
   2, and "mol" 3rd column.
Column 11, line 40, "ws" should be --was--.
Column 12, line 17, "per" should be --pre--.
Column 12, Title Column 1, "Axo" should be --Azo--.
```

UNITED STATES PATENT AND TRADEMARK OFFICE
CERTIFICATE OF CORRECTION

PATENT NO. : 4,153,687

DATED : May 8, 1979

INVENTOR(S) : Eugen Schnabel, et al.

It is certified that error appears in the above–identified patent and that said Letters Patent are hereby corrected as shown below:

```
Column 16, line 21, "inhitititors" should be --inhibitors--.
Column 16, Title Column 3, "Pancrease" should be
    --Pancreas--.
Column 17, Title, Column 3, "Pancrease" should be
    --Pancreas--.
Column 17, line 63, "=" should be -- ≙ --.
Column 18, line 63, "24.4)" should be --10.4- --.
Column 21, line 10, "radition" should be --radiation--.
Column 21, line 37, "cach" should be--each--.
Column 23, line 54, "M" should be --N--.
Column 24, line 19, "wre" should be --were--.
Column 26, line 10, "refraction" should be --fraction--.
Column 28, line 63, "ad" should be --as--.
```

UNITED STATES PATENT AND TRADEMARK OFFICE
CERTIFICATE OF CORRECTION

PATENT NO. : 4,153,687

DATED : May 8, 1979

INVENTOR(S) : Eugen Schnabel, et al.

It is certified that error appears in the above-identified patent and that said Letters Patent are hereby corrected as shown below:

Column 29, line 33, "disslved" should be --dissolved--.
Column 30, line 62 "82" should be -- μl --.
Column 30, line 68 "11" should be -- μl --.
Column 31, line 6, "4'" should be --4°--.
Column 31, line 40, "ml" should be --mg--.
Column 31, line 42, "asolution" should be --a solution--.
Column 32, line 37, "druying" should be --drying--.
Column 36, line 54, "carrid" should be --carried--.
Column 37, line 35, "desamine" should be --desamino--.
Column 38, line 42, "Oh" should be --OH--.
Column 38, line 54, "citracnylated" should be --citraconylated--.
Column 38, line 59, "Splitting.....groups" should start a new line

UNITED STATES PATENT AND TRADEMARK OFFICE
CERTIFICATE OF CORRECTION

PATENT NO. : 4,153,687

DATED : May 8, 1979

INVENTOR(S) : Eugen Schnabel, et al.

It is certified that error appears in the above-identified patent and that said Letters Patent are hereby corrected as shown below:

```
Column 39, line  4, "one" should be --once--.
Column 39, lines 35,36, "-dichloroaniline" should be
   --Example--.
Column 40, line 39, "carreid" should be --carried--.
Column 40, line 54, "elutting" should be --eluting--.
Column 40, line 57, " µ " second occurrence should be --µl --.
Column 42, line  9, "2" should be --0--.
Column 43, line  5, "an" should be --a--.
Column 43, line 61, "were" should be --was--.
Column 46, line 13, insert "tyrosine" after "21- ".
```

Signed and Sealed this

Twentieth Day of November 1979

[SEAL]

Attest:

RUTH C. MASON
Attesting Officer

LUTRELLE F. PARKER
Acting Commissioner of Patents and Trademarks